US009555049B2

(12) United States Patent
Contel et al.

(10) Patent No.: US 9,555,049 B2
(45) Date of Patent: Jan. 31, 2017

(54) ARENE RUTHENIUM (II) DERIVATIVES CONTAINING IMINOPHOSPHORANE LIGANDS AND THEIR USE IN CANCER THERAPY

(71) Applicant: Research Foundation of the City University of New York, New York, NY (US)

(72) Inventors: Maria Contel, Brooklyn, NY (US); Isabel Marzo, Zaragoza (ES); Malgorzata Frik, Glendale, NY (US); Benelita T. Elie, Brooklyn, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 14/724,274

(22) Filed: May 28, 2015

(65) Prior Publication Data

US 2015/0374724 A1     Dec. 31, 2015

Related U.S. Application Data

(60) Provisional application No. 62/016,796, filed on Jun. 25, 2014.

(51) Int. Cl.
*A61K 31/66* (2006.01)
*A61K 31/675* (2006.01)

(52) U.S. Cl.
CPC ............. *A61K 31/66* (2013.01); *A61K 31/675* (2013.01)

(58) Field of Classification Search
None
See application file for complete search history.

(56) References Cited

PUBLICATIONS

Morris et al., Inhibition of Cancer Cell Growth by Ruthenium(II) Arene Complexes, 2001, J. Med. Chem., 44, pp. 3616-3621.*
Biswas et al., Asymmetric cleavage of 2,2'-pyridil to a picolinic acid anion radical coordinated to ruthenium(II): splitting of water to hydrogen, 2013, Chem. Commun., 49, pp. 4522-4524.*
Cadierno et al., Iminophosphorane-Based Nucleophilic Ruthenium (II) Carbene Complexes: Unusual C—C Coupling and C—H Activation Promoted by the Addition of Alkynes to Ru=C Bond, 2005, Organometallics, 24, pp. 2801-2810.*
Frik, Malgorzata et al; In Vitro and In Vivo Evaluation of Water-Soluble Iminophosphorane Ruthenium(II) Compounds. A Potential Chemotherapeutic Agent for Triple Negative Breast Cancer; J. Med. Chem; 2014; 57, 9995-10012.
Nazarov, Alexey A. et al; Opening the lid on piano-stool complexes: An account of ruthenium(II)-arene complexes with medicinal applications; Journal of Organometallic Chemistry 751 (2014) 251e260.
Bergamo, A. et al; In vivo tumour and metastasis reduction and in vitro effects on invasion assays of the ruthenium RM175 and osmium AFAP51 organometallics in the mammary cancer model; Journal of Inorganic Biochemistry 104 (2010) 79-86.
Scolaro, Claudine et al.; In Vitro and In Vivo Evaluation of Ruthenium(II)-Arene PTA Complexes; J. Med. Chem. 2005, 48, 4161-4171.
Adhireksan, Zenita et al.; Ligand substitutions between ruthenium-cymene compounds can control protein versus DNA targeting and anticancer activity; Feb. 18, 2014; Nature Communications; DOI: 10.1038/ncomms4462.
Aguilar, David et al; Cycloruthenated Complexes from Iminophosphoranes: Synthesis, Structure, and Reactivity with Internal Alkynes; Organometallics; 2011; 30, 642-648.

* cited by examiner

*Primary Examiner* — Kortney L Klinkel
*Assistant Examiner* — Tori M Strong
(74) *Attorney, Agent, or Firm* — Peter J. Mikesell; Schmeiser, Olsen & Watts, LLP

(57) ABSTRACT

A method for providing a therapeutic benefit for a subject having a cancer is provided. A compound with an arene ruthenium (II) compound with an iminophosphorane ligand is administered to the subject.

10 Claims, 9 Drawing Sheets

ARENE RUTHENIUM (II) DERIVATIVES CONTAINING IMINOPHOSPHORANE LIGANDS AND THEIR USE IN CANCER THERAPY

CROSS-REFERENCE TO RELATED APPLICATIONS

This application claims priority to and the benefit of co-pending U.S. provisional patent application Ser. No. 62/016,796 (filed Jun. 25, 2014) which application is incorporated herein by reference in its entirety.

STATEMENT REGARDING FEDERALLY FUNDED RESEARCH OR DEVELOPMENT

This invention was made with government support under contract number 5SC2GM082307 awarded by the National Institute of Health-National Institute of General Medical Science (NIH-NIGMS) and contract number 1SC1CA182844 awarded by the National Institute of Health-National Cancer Center (NIH-NCI). The government has certain rights in the invention.

BACKGROUND

Of the estimated 1 million cases of breast cancer diagnosed worldwide in 2008, it is estimated that 172,695 harbored the triple-negative phenotype. Triple-negative breast cancer is currently receiving a tremendous and appropriate amount of research attention given its unique biology, overall poor prognosis, aggressive and early pattern of metastases and relative lack of therapeutic targets when compared with endocrine-sensitive and HERK-2 positive breast cancers. There is a clear need to increase the number of chemotherapeutic options for this and other types of breast cancer.

Metallo-drugs are important tools in current cancer therapy. Platinum-derived drugs are commonly used, particularly for the treatment of testicular and ovarian cancers, but have failed in breast cancers. In addition, the toxicity of Pt derivatives has prompted the search for alternative metallo-drugs. In the search for metal-based chemotherapeutics with improved properties with respect to platinum-based drugs used in the clinic, ruthenium compounds have emerged as promising candidates.

Ruthenium complexes have certain characteristics which make them attractive as potential chemotherapeutics for different diseases. Ruthenium metal compounds can easily access multiple oxidation states (II, III and possibly IV) in biological fluids. Ruthenium (III) compounds could potentially behave as pro-drugs as they can be reduced to ruthenium (II) derivatives in solid tumor masses where the high content in oxygen may act as a reducing environment. As platinum-based drugs, ruthenium compounds can exchange N and O-donor molecules with the added advantage of the possibility of forming octahedral complexes (of interest in reactions with DNA). Ruthenium derivatives probably use transferrin to accumulate into tumors due to the similarities with iron. The lower toxicity when compared to cisplatin and platinum based compounds of ruthenium compounds and their cytotoxic and/or antimestastatic properties has resulted in two ruthenium(III) compounds (NAMI-A and KP1019) having entered clinical trials (phase I and II). These compounds are about to be commercialized as a second line therapy in combination with gemcitabine in the treatment of NSCLC (NAMI-A) and for colorectal cancer (KP1019).

While the use of ruthenium-based chemotherapeutic have proven successful for some forms cancer, there is still a desire for different chemotherapeutics and particularly chemotherapeutics useful against triple negative breast cancer.

SUMMARY OF THE INVENTION

A method for providing a therapeutic benefit for a subject having a cancer is provided. A compound with an arene ruthenium (II) compound with an iminophosphorane ligand is administered to the subject.

In a first embodiment, a method for providing a therapeutic benefit for a subject having a cancer is provided. The method comprises administering to the subject a compound of Formula (A), a steroisomer, geometric isomer or pharmaceutically acceptable salt or pro-drug therefor, the compound comprising an arene ruthenium (II) compound with a iminophosphorane ligand. Formula (A):

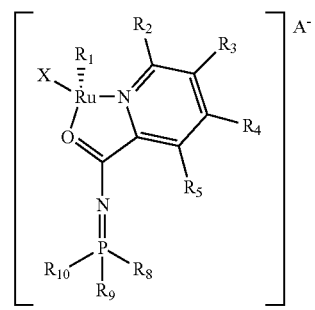

wherein: X is a halogen; A⁻ is an anion; $R_1$ is an arene; $R_2$, $R_3$, $R_4$ an $R_5$ are independently selected from the group consisting of a hydrogen and a $C_1$-$C_5$ alkyl; $R_8$, $R_9$ and $R_{10}$ are independently selected from a $C_1$-$C_5$ alkyl, an arene, and a cyclic amine.

In a second embodiment, a method for providing a therapeutic benefit for a subject having a cancer is provided. The method comprising administering to the subject a compound of Formula (A), a steroisomer, geometric isomer or pharmaceutically acceptable salt or pro-drug therefor, the compound comprising an arene ruthenium (II) compound with a iminophosphorane ligand. Formula (A)

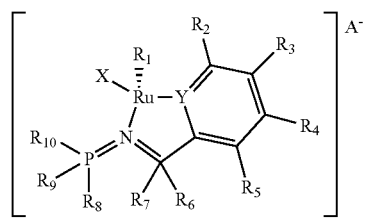

wherein: X is a halogen; A⁻ is an anion; Y is carbon or nitrogen; $R_1$ is an arene; $R_2$, $R_3$ and $R_4$ are independently selected from the group consisting of a hydrogen and a $C_1$-$C_5$ alkyl; $R_5$ is a hydrogen or forms a ring with $R_6$; $R_6$ is a hydrogen, is a ketone or forms the ring with $R_5$; $R_7$ is a hydrogen, is the ketone or forms the ring with $R_5$; $R_8$, $R_9$ and $R_{10}$ are independently selected from a $C_1$-$C_5$ alkyl, an arene, and a cyclic amine.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
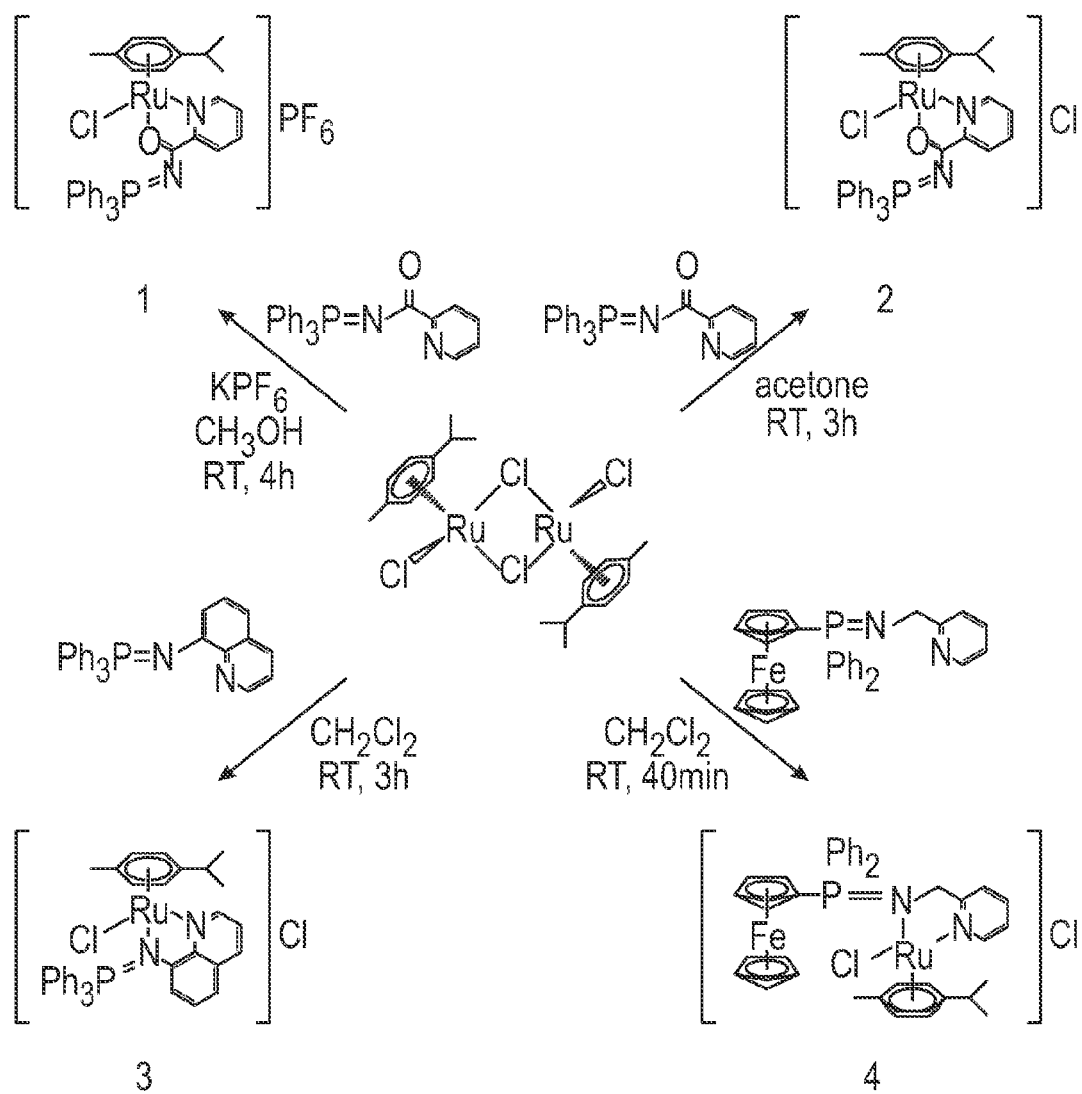
FIG. 1 is a synthetic scheme depicting the preparation of cationic ruthenium (II) compounds containing IM ligands.

Disclosed in this specification are compounds and methods useful as chemotherapeutics for cancers, including triple negative breast cancer. This disclosure deals with the preparation of new arene ruthenium (II) compounds containing iminophosphorane ligands as anticancer chemotherapeutics for the treatment of different cancers and more specifically for the treatment of triple negative breast cancer. The disclosed compositions may also be useful as homogenous water soluble catalysts in chemical reactions of industrial interest such as hydrogen transfer or hydrogenation.

In one embodiment, the disclosed organometallic ruthenium (II) complexes comprise iminophosphorane ligands and are of the type [η⁶-p-cymene)(Ru(IM-k-N,O)Cl]A where IM is $PH_3P=N-CO-2-N-C_5H_4$ and A is $PF_6^-$ (compound 1) or $Cl^-$ (compound 2).

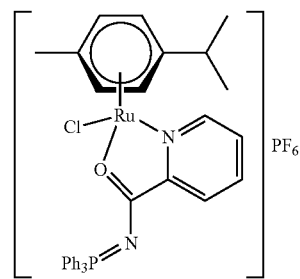

1

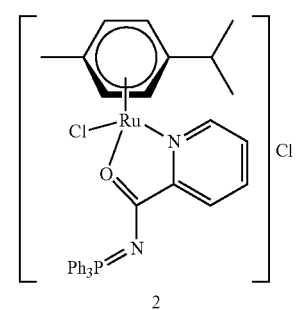

2

In another embodiment, the disclosed complexes are of the type [η⁶-p-cymene)Ru(IM-k-N,N)Cl]Cl where IM is $PH_3P=N-8-C_9H_6N$ (compound 3) or [Cp-P(Ph₂)=N—$CH_2$-2-$NC_5H_4$}Fe(Cp)] (compound 4).

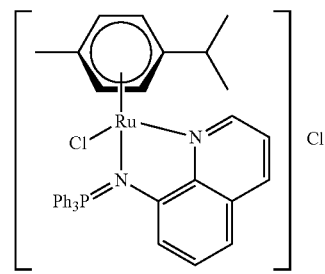

3

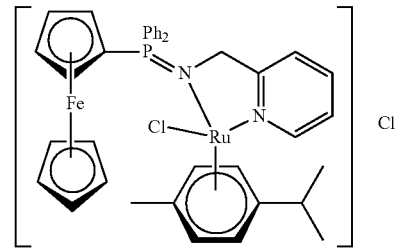

4

In another embodiment, the disclosed complexes are of the type [η⁶-p-cymene)(Ru(IM-k-C,N)Cl]IM where IM is $PH_3P=N-CO-2-C_6H_4$ (compound 8) or [η⁶-p-cymene) (Ru(IM-k-C,N)Cl]TPA where TPA is 1,3,5-triaza-7-phosphaadamantane (compound 9).

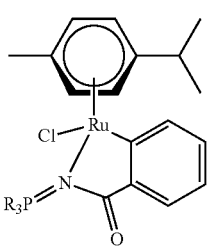

PR₃ = PPh₃ (8), TPA (9)

The halogen-containing compounds 2, 3, 4 8 and 9 all have good solubility in water (70-100 mg per mL). All compounds were air stable. The complexes have been evaluated for their antiproliferative properties in human cancer cell lines (leukemia Jurkat-T, lung A459, prostate DU-145, pancreas MiaPaca, and triple negative breast MDA-MB-231) and in a non-tumorigenic human embryonic kidney cell line (HEK-293T). Most of these compounds are more cytotoxic to these cancer cell lines than cisplatin. Additionally, the highly water-soluble compound 2 was significantly more cytotoxic than cisplatin to lung A459, prostate DU-145, colon MiaPaca2, and triple negative breast MDA-MB-231 cancer cell lines ($IC_{50}$ values 12 to 72 times lower than those for cisplatin). The toxicity of compound two was evaluated in human renal proximal tubular cell lines (RPTC cell lines) as an in vitro model for nephrotoxicity. Importantly, it was found that compound 2 was less toxic to RPTC cell lines than to the cancer cell lines studied.

Initial mechanistic studies suggest the cell death type for compound 2 and compound 3 is mainly through canonical or caspase-dependent apoptosis. In addition, the cell death does not appear to depend on p53. Only the compound 1 and the compound 2 show interaction with plasmid (pBR322) DNA but it seems weak and electrostatic in nature. Compound 2 does not inhibit protease capthesin B in concentrations of 100 μM or lower. Compound 2 was selected for in vivo experiments to evaluate its antitumor properties on MDA-MB-231 xenografts in NOD.CD17-Prkdc scid/J mice. An impressive tumor reduction (shrinkage) of 54% was observed after 21 days treatment (11 doses of 5 mg per kg every other day) with low systemic toxicity at this dose.

FIG. 1 is a schematic depiction of a synthetic scheme of compounds 1-4 from $[(\eta^6\text{-p-cymene})Ru(\mu\text{-Cl})Cl]_2$.

Figure 2:
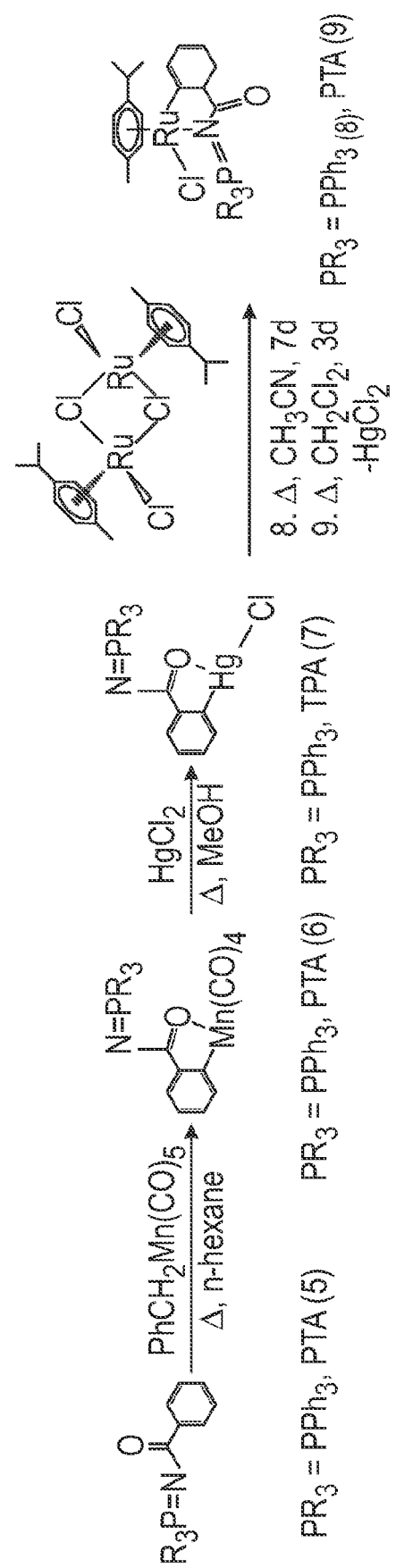
FIG. 2 is a synthetic scheme depicting the preparation of cycloruthenated compounds containing IM ligands.

FIG. 2 is a schematic depiction of a synthetic scheme of compounds 8-9 that have cyclometallated IM (pincer, C,N—) ligands using transmetallation with organomercury derivatives. The nature of the IM ligand played an important role and compounds with stabilized IM ligands containing carbonyl groups (e.g. 2-$C_6H_4$)$Ph_2P$=N—CO—Ph) proved difficult to synthesize. Cycloruthenated compounds were prepared in which the aryl group of the imino fragment is coordinated to the metal center (exo derivatives) as opposed to an aryl group of the phosphine fragment (endo derivatives) in order to be able to incorporate different phosphines into the final molecule. This permitted electronic/steric properties of the resulting complexes to be tuned. Intermediate Hg($Ph_3P$=N—CO-2-$C_6H_4$)Cl was utilized. The C—H activation at the N—CO-pH fragment takes place at a manganese center and by transmetallation of the resulting cyclometalated iminophosphorane manganese compounds to $HgCl_2$. The organomercury derivatives with $PPh_3$[Hg($Ph_3P$=N—CO-2-$C_6H_4$)Cl] or water soluble phosphine PTA[Hg(PTA=N—CO-2-$C_6H_4$)Cl] (compound 7) are obtained in high yields. Transmetallation reactions of [Hg($Ph_3P$=N—CO-2-$C_6H_4$)Cl] and compound 7 with $[(\eta^6\text{-p-cymene})Ru(\mu\text{-Cl})Cl]_2$ afford new cyclometallated compound 8 or compound 9 in high yield.

Structures from compounds 1, 2, 3, 4, 9 and 9 were determined on the basis of analytical (elemental analysis), spectroscopic (IR and NMR), conductivity and MS spectrometry data. The IM ligand in compound 1 and compound 2 is bonded as a chelate giving a fac-Cl,N,O arrangement while in compound 3 and compound 4 the arrangement is fac-Cl,N,N. This can clearly inferred from IR data. A strong absorption at 1531 $cm^{-1}$ is present due to vCO stretch for compound 1 and compound 2 shifted to lower wavenumbers with respect to that of the free ligand at 1598 $cm^{-1}$. For compound 3 and compound 4 the signal associated with a vPN stretch is shifted to lower wavenumbers respective to that of the free ligand. Signals in $^{31}P\{^1H\}$ NMR are strongly shifted to low field with respect to free ligands, indicating iminic N-bonding. The ortho protons for the quinonline ($H_2$) and pyridine ($H_6$) in the $^1H$ NMR spectra for compound 3 and pyridine ($H_6$) for compound 4 are shifted downfield, evidencing N-coordination.

Figure 3:
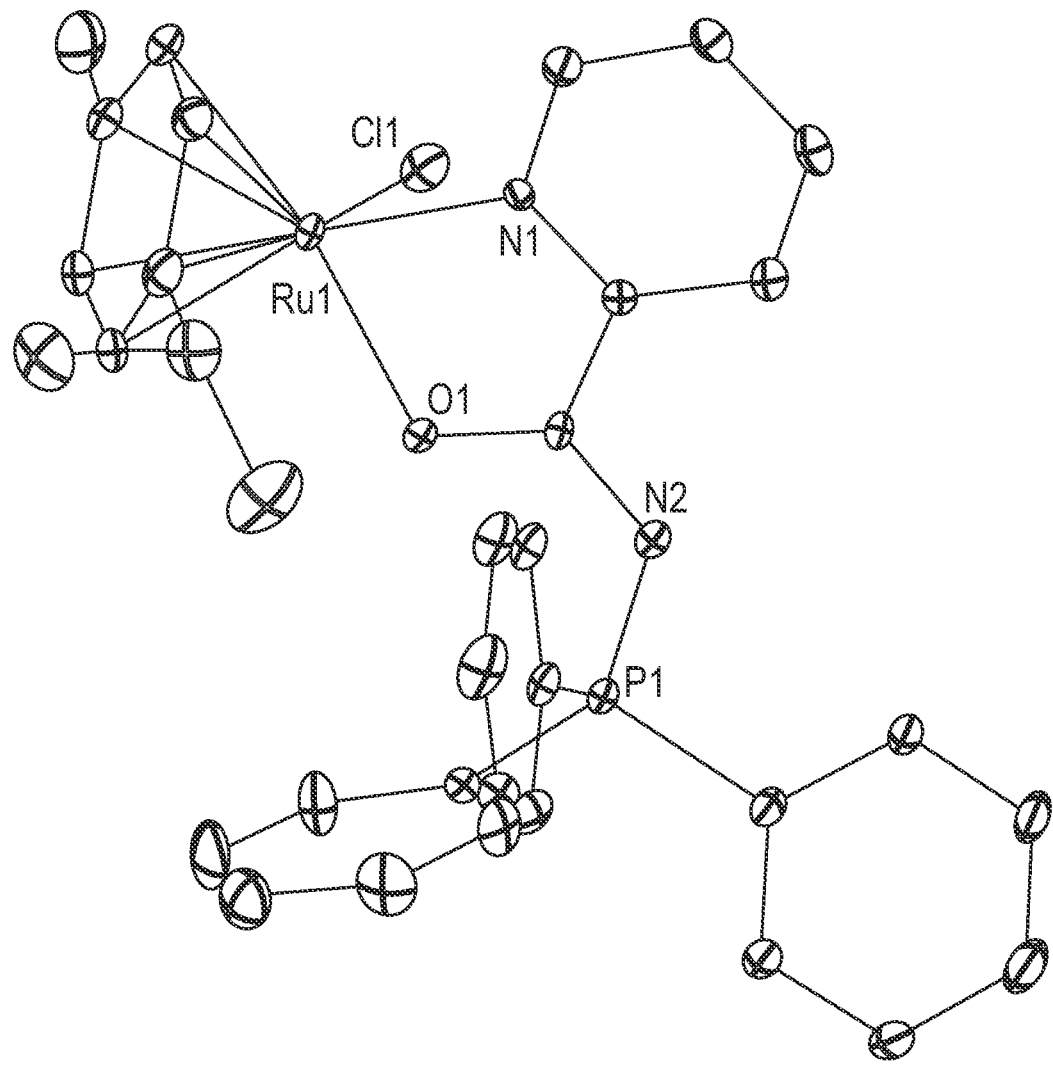
FIG. 3 is a molecular structure diagram of compound 1.

As shown in FIG. 3, the structure of compound 1 has been obtained by X-ray analysis. The piano-stool around the ruthenium center, as well as the coorination of the Im ligand through the N and O atoms, is confirmed. Select distances [Å] and angles [deg]: Ru(I)—O(1) 2.110(3); Ru(1)-N(1) 2.095(4); Ru(1)-C(10) 2.153(5); Ru(1)-C(6) 2.154(5); Ru(1)-C(7) 2.171(5); Ru(1)-C(9) 2.187(5); Ru(1)-C(11) 2.191(5); Ru(1)-C(8) 2.204(5); Ru(1)-Cl(1) 2.3775(14); O(1)-C(16) 1.266(6); C(1)-N(2) 1.337(7); C(1)-C(2) 1.385(8); N(2)-P(1) 1.619(5); N(1)-Ru(1)-O(1) 76.68(14); O(1)-Ru(1)-Cl(1) 83.61(10); N(1)-Ru(1)-Cl(1) 83.13(12).

Compound 8 and compound 9 are cycloruthenated neutral species with the IM ligand in an exo disposition [$\eta^6$-p-cymene)(Ru(IM-k-C,N)] (IM=$Ph_3P$=N—CO-2-$C_6H_4$ compound 8; TPA=N—CO-2-$C_6H_4$ compound 9). Their $^1H$ NMR spectra show the presence of signals due to $\eta^6$-arene as well as the $C_6H_4P$ units. In addition, the $^{13}C\{^1H\}$ NMR shows six well-resolved peaks due to the $C_6H_4P$ unit. The signals in the $^{31}P\{^1H\}$ NMR spectra are strongly shifted downfield with respect to those for the free ligand.

The cationic compounds with chloride as counterion (compounds 2, 3, and 4) are highly soluble in water (solubility ranging from 70 to 100 mg/mL). The cycloruthenated derivative with a water-soluble phosphine TPA (compound 9) is much less soluble in water (solubility 1 mg per ml, compound 9). Compound 1, and cyclorutenated compounds 8 and 9 are soluble in mixtures 1:99 DMSO:$H_2O$ in micromolar concentrations.

Compounds 1, 2, 3, 4 and 8 are stable for weeks in $d^6$-DMSO solution. The stability of the water-soluble complexes was studied by $^{31}P\{^1H\}$ and $^1H$ NMR spectroscopy in $D_2O$. The spectra in $D_2O$ for compound 4 does not change for over three days but after that time the compound precipitates. The $^{31}P\{^1H\}$ NMR spectra in $D_2O$ for compound 3 (δ=37.73 ppm) shows an additional signal (δ=38.34 ppm) right away that may be assigned to hydrolyzed species of the type $[(\eta^6\text{-p-cymene})Ru(Ph_3P=N\text{-}8\text{-}C_9H_6N)(OH_2)]^{2+}$. The integration of these signals is ca. 45:55 and the spectra does not change significantly over time (days). In the case of compound 2 (δ in $D_2O$ 26.33 ppm) this signal (attributable to $[(\eta^6\text{-p-cymene})Ru(Ph_3P=N\text{—CO-2-N—}C_5H_4)(OH_2)]^+$ is also visible in $D_2P$ (δ=26.65 ppm) along with another signal (δ=43.79 ppm) which may correspond to the cyclometalated species $[(\eta^6\text{-p-cymene})Ru(IM\text{-}k\text{-}C,N\text{—}C_6H_4(PPh_2=N\text{—CO-2-N—}C_5H_4)Cl]$ or $[(\eta^6\text{-p-cymene})Ru(IM\text{-}k\text{-}C,N\text{—}C_6H_4(PPh_2=N\text{—CO-2-N—}C_5H_4)(OH_2)]^+$ and that grows overtime. The half-life for compound 2 in $D_2O$ is three days. The cyclometalation process for compound 2 seems to proceed faster in a 100 mM NaCl solution in $D_2O$ (half-life ca. 10 hours at 14.5 mM of compound 2) and by increasing the temperature (60% after 1 hour at 80° C.). However, as explained elsewhere in this specification, the biological activity of compound 2 is very fast (in 8 hours compound 2 induces 80% of apoptosis on Jurkat cells). Thus, without wishing to be bound to any particular theory, the observed biological activity is believed to mainly come from coordination compound 2 or its hydrolysis product.

The antiproliferative properties of the new ruthenium compounds 1-4, 8 and 9 and starting material $[(\eta^6\text{-p-cymene})Ru(\mu\text{-Cl})Cl]_2$ were assayed by monitoring their ability to inhibit cell growth using the MTT assay. Cytotoxic activity of the compounds was determined in some human cancer cell lines: leukemia Jurkat-T, lung A549, prostate DU-145, pancreas MiaPaca2, and triple negative breast MDA-MB-231, in comparison to cisplatin. The results are summarized in Table 1.

MiaPaca2 cancer cell line and to the breast cancer MDA-MB-231 cell line than to HEK293T although the $IC_{50}$ for those cell lines are higher than other compounds in Table 1.

Importantly as HEK cell lines are immortalized cells that can display a higher sensitivity to chemicals, the effect of compound 2 on human renal proximal tubular cells (RPTC) were measured. Renal proximal tubular cells in primary culture have been described as an in vitro model to study nephrotoxicity. The $IC_{50}$ value (XTT assay 24 hours) for compound 2 in this cell line was 13.84±1.46 µM (value obtained for cisplatin as control was 46.42±2.46 µM). Thus compound 2 is more toxic to all cancer cell lines than to the "healthy" human renal cell line and markedly more toxic to the leukemia Jurkat-T (17.7-fold), prostate DU145 (9-fold), triple negative breast cancer MDA-MB-231 (5.3-fold), and pancreas MiaPaca (4.7-fold) cancer cell lines.

Compound 2 with an IC50 of 2.64 µM is 30 times more cytotoxic in MDA-MB-231 breast cancer cell lines than compound RM175 with an IC50 of 62 µM under the same conditions (MTT, 24 h incubation). The toxicity of RM175

TABLE 1

IC50 (µM) of metal complexes 1-4, 8-9, $[(\eta^6\text{-p-cymene})Ru(\mu\text{-Cl})Cl]_2$[a] and cisplatin in human cell lines[b, c]

| Compound | Jurkat | A549 | DU-145 | MiaPaca2 | MDA-MB-231 | HEK-293T |
|---|---|---|---|---|---|---|
| 1 | 1.1 ± 0.14 | 9.9 ± 1.9 | 1.89 ± 0.64 | 2.4 ± 0.18 | 4.91 ± 2.7 | 2.8 ± 0.2 |
| 2 | 0.78 ± 0.08 | 9.5 ± 2.1 | 1.55 ± 0.21 | 2.9 ± 0.8 | 2.61 ± 1.2 | 2.8 ± 0.2 |
| 3 | 0.9 ± 0.32 | 43.3 ± 8.0 | 6.6 ± 0.85 | 7.0 ± 0.4 | 16.2 ± 0.9 | 2.2 ± 1.1 |
| 4 | 9.3 ± 0.07 | >125 | 148 ± 33 | >125 | >125 | 114.5 ± 14.8 |
| 8 | 2.39 ± 0.27 | 29.9 ± 5.8 | 14.2 ± 4.2 | 8.2 ± 0.98 | 7.1 ± 0.11 | 4.1 ± 0.06 |
| 9 | 17.7 ± 7.5 | >125 | 125.5 ± 28 | 54.5 ± 16 | 75.4 ± 9.8 | 141.9 ± 13.1 |
| Cisplatin | 10.8 ± 1.2 | 114.2 ± 9.1 | 112.5 ± 33 | 76.5 ± 7.4 | 131.2 ± 18 | 69.0 ± 6.7 |

[a]$IC_{50}$ for $[(\eta^6\text{-p-cymene})Ru(\mu\text{-Cl})Cl]_2$ >125 µM for all cel lines.
[b]Data are expressed as mean ± SD (n = 4).
[c]All compounds were dissolved in 1% of DMSO and diluted with water before addition to cell culture medium for a 24 h incubation period. Cisplatin was dissolved in water.

The starting material $[(\eta^6\text{-p-cymene})Ru(\mu\text{-Cl})Cl]_2$ is poorly cytotoxic in all tested cell lines ($IC_{50}$ greater than 125 µM). The 1M ligands coordinated to the ruthenium centers are known to be poorly cytotoxic ($IC_{50}$ in different cell lines greater than 100-500 µM).

Compounds 1-3 with coordinated IM ligands and compound 8 with a IM—$PPh_3$ cyclometalated ligand were considerably more cytotoxic than cisplatin in all the cell lines studied. Compounds 1 and 2 (same cation) display almost identical $IC_{50}$ values but compound 2 is soluble in $H_2O$. Compound 4, based on an iminophosphorane ligand containing a ferrocenyl phosphine Fe—Ru, was less cytotoxic than cisplatin. Dimetallic compounds Fe—Au and Fe—Pd had higher $IC_{50}$ values when compared to trimetallic derivatives or compounds with different IM ligands. The cycloruthenated compound containing a water soluble IM ligand (IM-TPA) was more cytotoxic than cisplatin for the pancreas MiaPaca2, and triple negative breast MDA-MB-231 cell lines.

In order to assess the compounds' selectivity for cancerous cells with respect to normal cell lines, the compounds were also screened for their antiproliferative effects on the non-tumorigenic human embryonic kidney cells HEK293T. In most cases the cytotoxicity was comparable for the cancerous and HEK293T cells. All compounds were more toxic to leukemia cell lines than to HEK293T celllines (2 to 8 times) and compounds 1, 2, and 9 are more toxic to prostate DU-145 cancer cell line than to HEK cell lines. In addition, compound 9 is more toxic to the pancreas in HBL100 human epithelial cell lines (IC50=54 µM) was similar to that in breast cancer cell lines. The toxicity of compound 2 in the MDA-MB-231 cell lines in vitro is similar to that of the type $[Ru(Cp)(2,2\text{-bipy})(PR_3)][CF_3SO_3]$. These compounds, which revealed fast antiproliferative effects at short incubations time like some compounds described here, have shown to interact weekly with DNA. They can inhibit lactate production and TPMET (trans-plasma-membrane electron transport) in a way dependent on the cancer cell aggressiveness and the concentration of the complex.

Figure 4A:
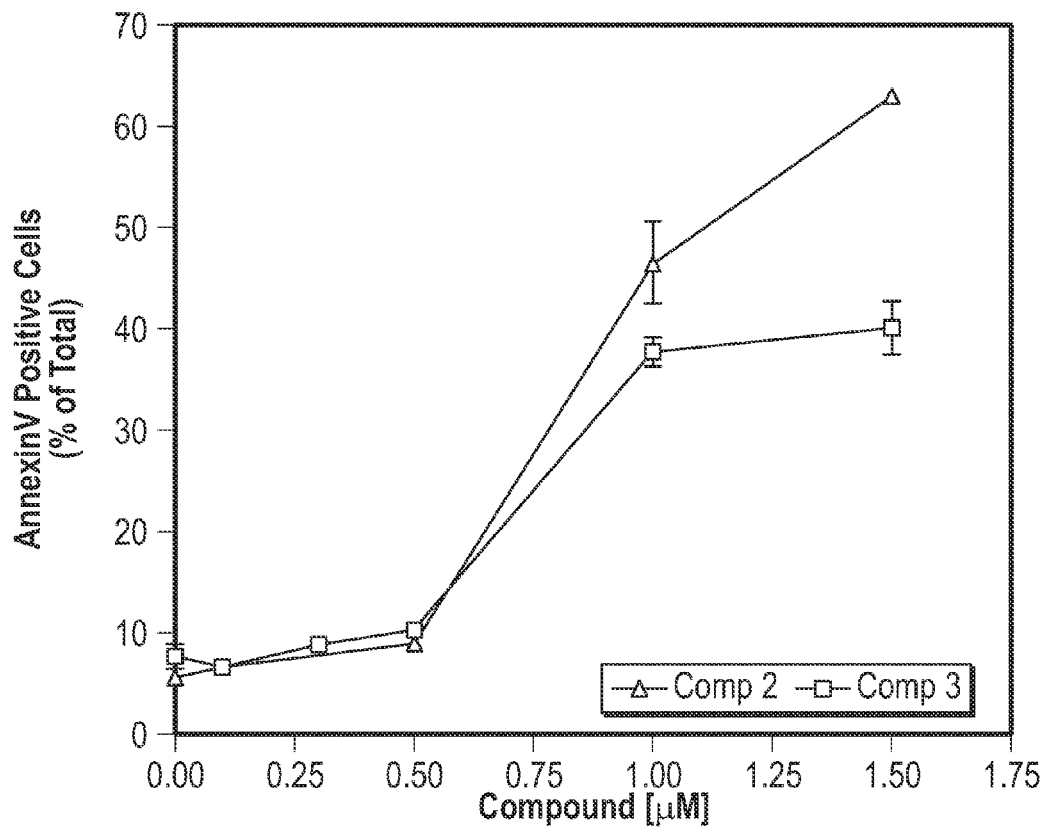
FIG. 4A is a dose-response quantification of time-course analysis of PS exposure caused by compound 2 and compound 3 in Jurkat cells.
Figure 4B:
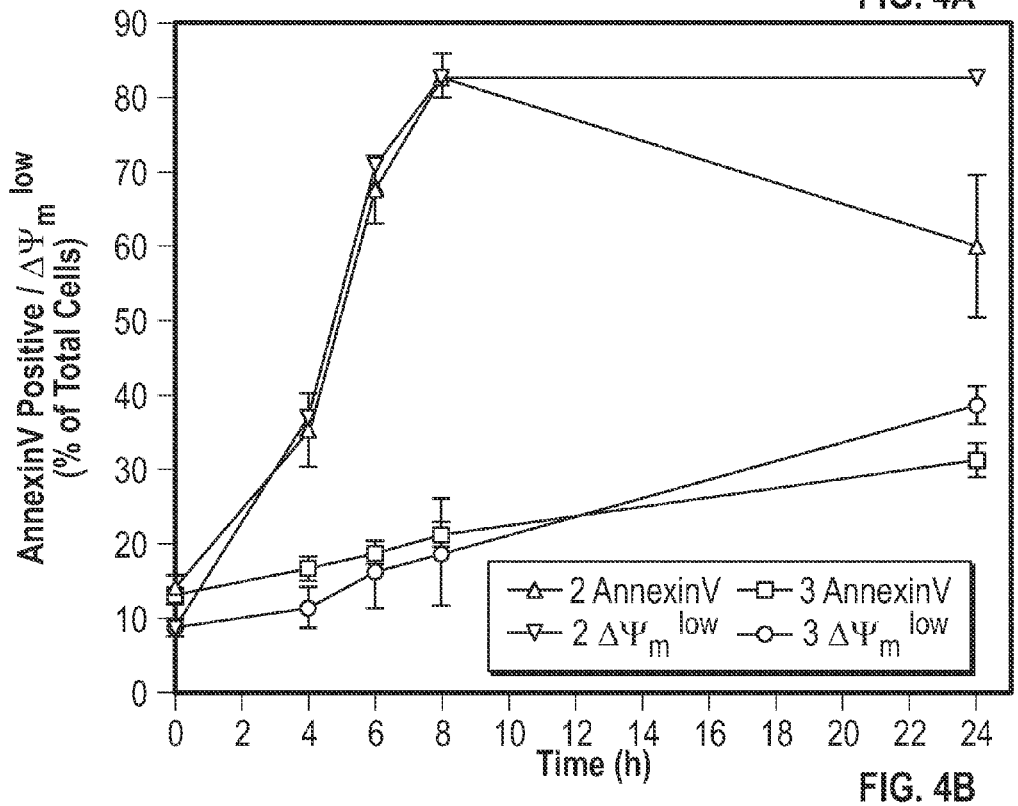
FIG. 4B is a dose-response quantification of PS exposure and $\Delta\psi_m$ loss caused by compound 2 and compound 3 in Jurkat cells.
Figure 5:
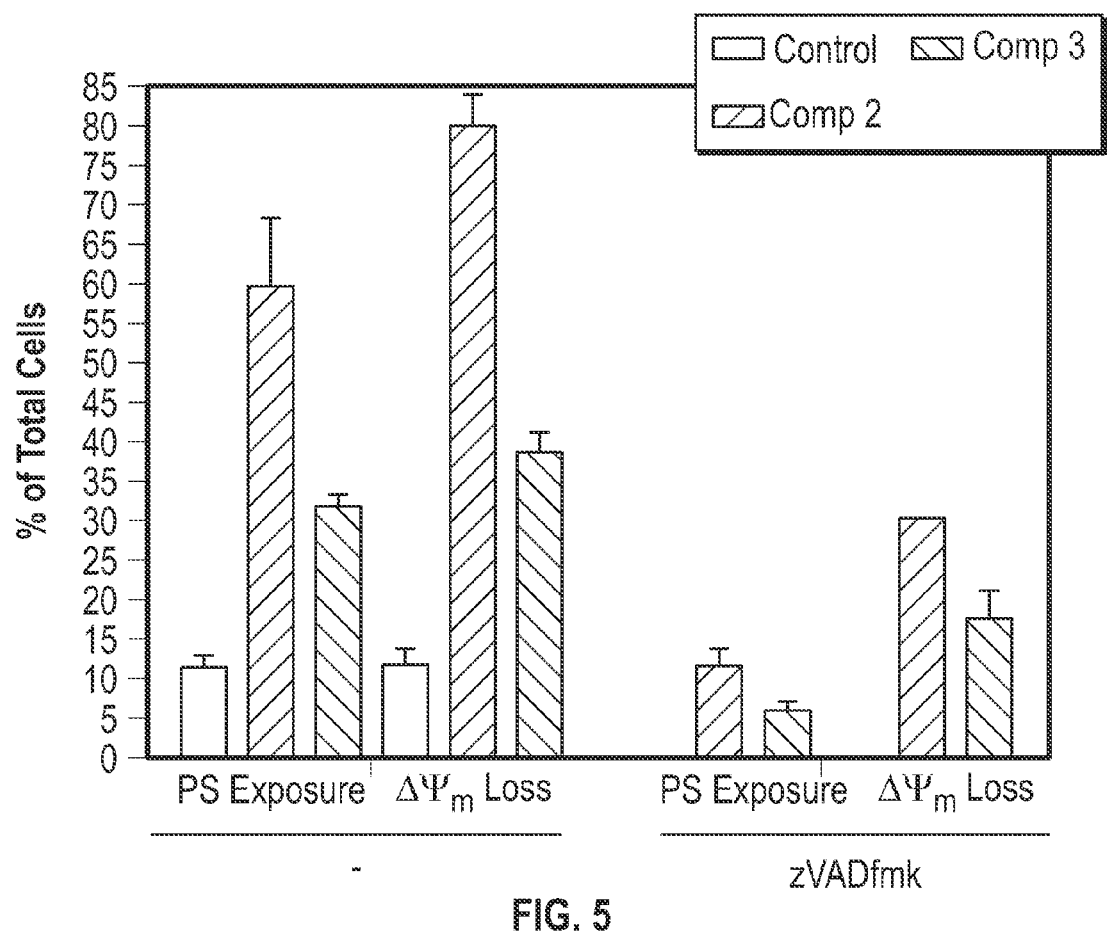
FIG. 5 is a graph depicting the effect of general capase inhibitor z-VAD-fmk in apoptotic features induces by compound 2 and compound 3.

The mechanism of cell death induced by compound 2 and compound 3 was explored in Jurkat cells. Nuclei morphology after twenty-four hour incubation with 1 µM solution of compound 2 or compound 3 was analyzed by Hoechst staining. Typical apoptotic features, chromatin condensation and fragmentation, were detected. Other apoptotic parameters such as phosphatidylserine exposure and mitochondrial membrane potential dissipation were analyzed using fluorescent probes. Dose-response experiments (FIG. 4A) confirmed that compound 2 is more cytotoxic than compound 3, as also indicated by MTT assays. Time-course experiments indicated that compound 2 induced apoptosis in around 80% of cells after eight hours treatment (FIG. 4B). Trypan blue staining confirmed that cell death was through apoptosis, with very low secondary necrotic cells at six hours. Phosphatidylserine exposure and loss of transmembrane mitochondrial potential occurred in the same percentage of cells, although at longer incubation periods, there was an apparent decrease in the percentage of AnnexinV positive cells that was in fact due to cell disintegration. Apoptosis induction was slower for compound 3 with the percentage of both AnnexinV$^+$ and $\Delta\psi_m^{low}$ cells gradually increasing during the twenty-four hour period of the experiments (FIG. 4B). Taken together these results pointed to a classical apoptosis mechanism of cell death. This was confirmed by the finding that the cytotoxicity of both compounds was caspase-dependent (FIG. 5). The general caspase inhibitor z-VAD-fmk completely abrogated PS exposure but it only partially reduced $\Delta\psi_m$ loss (from 80% to 30% for compound 2 and from 40% to 20% for compound 3).

Figure 6:
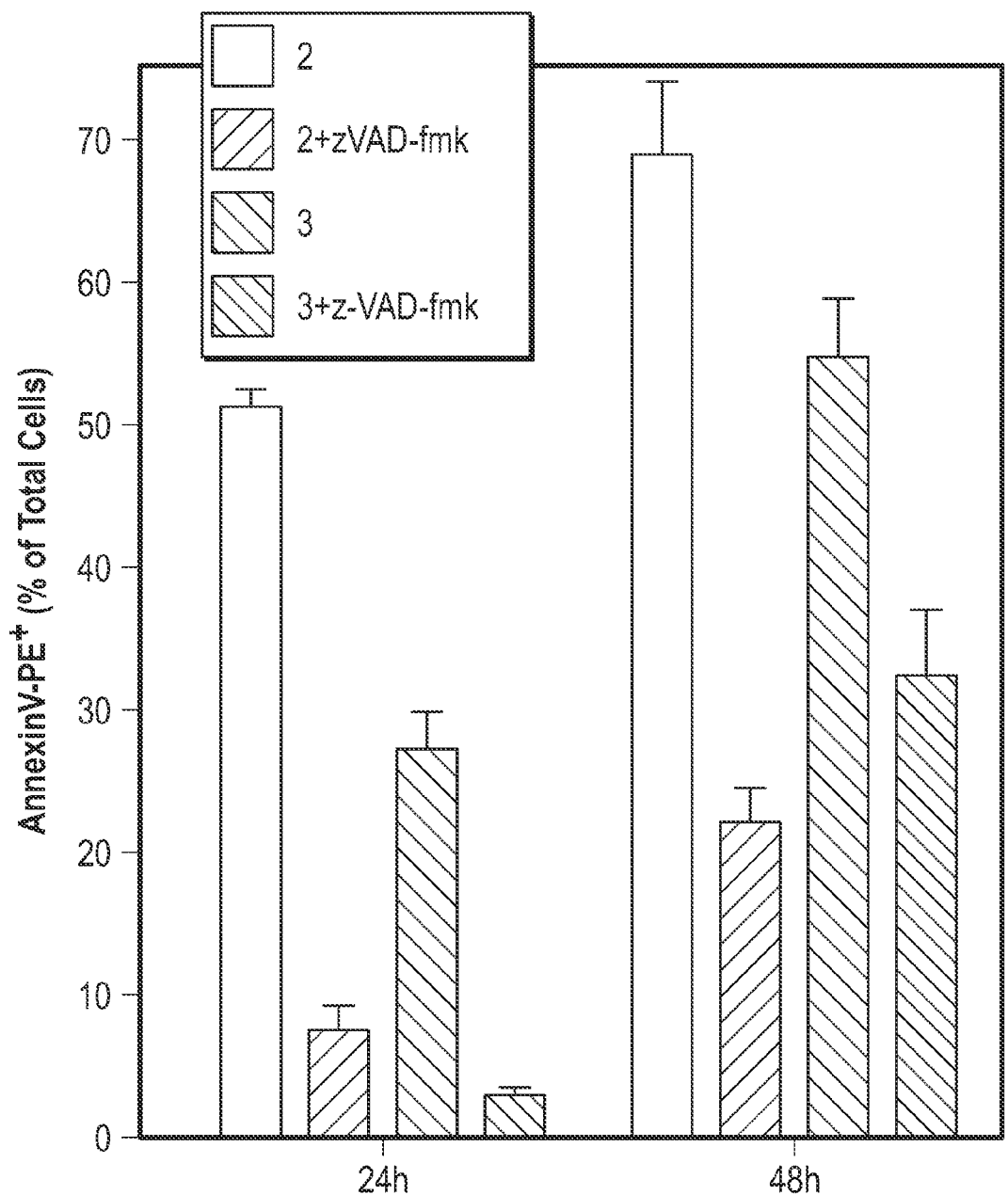
FIG. 6 is a graph depicting an analysis of long-term protection by z-VAD-fmk.

Because $\Delta\psi_m$ disruption was not completely inhibited by z-VAD-fmk, compound 2 and compound 3 might activate caspase-independent pathways acting on mitochondria. To determine whether caspase inhibition prevented or just delayed cell death, experiments were performed in which cells were treated with compound 2 or compound 3 for twenty-four hours in the presence of z-VAD-fmk and then washed and further cultured in fresh medium for twenty-four hours (FIG. 6). PS exposure was analyzed after the first twenty-four hours in the presence of compound+z-VAD-fmk and twenty-four hours after washing. Only around 20% of cells were AnnexinV$^+$ after twenty-four hours incubation with compound 2+z-VAD-fmk and twenty-four hours in fresh medium, while 70% of cells treated with compound 2 alone were apoptotic at the end of the experiments. Thus, these results indicate that in the case of compound 2, caspase inhibition prevented death commitment in a very high percentage of cells because only 22% were AnnexinV$^+$ twenty-four hours after washing. However, in the case of compound 3, the percentage of AnnexinV$^+$ cells twenty-four hours after washing (32%) equaled that of cell treated with compound 3 alone for twenty-four hours (28%) suggesting that, in this case, caspase inhibition did not prevent irreversible cell damage leading to cell death. These results suggest that compound 2 and compound 3 could be acting through different mechanisms, with compound 3 causing caspase-independent premitochondrial damage. These differences in the mechanism of compound 2 and compound 3 could explain why compound 3 is less selective than compound 2 for tumor cell lines (Table 1).

To determine whether the cytotoxicity of the compounds described herein is p53-dependent the levels of p53 in A549 cells, bearing wt-p53, were analyzed after a short-term treatment with compound 2. Treatment with compound 2 did not induce the stabilization of p53, and even at three and 6 hours a slight decline in p53 levels was observed, probably due to cell death and protein loss. These results differ from that reported with other ruthenium organometallic compounds that induce short-term p53 accumulation. However, although p53 protein is induced by RM175 in HCT116 (colon carcinoma) or RDC-9 in A172 (glioblasto-ma) and HCT116, genetic inhibition of p53 does not avoid the cytotoxicity of these compounds, clearly indicating that other p53-independent mechanisms can be activated by ruthenium compounds. Moreover, a p53$^{-/-}$ cell line (TK6) is known to exhibit the same sensitivity to RDC-9 than its p53$^{+/+}$ parental cell line (NH32). Furthermore, compounds 1-3 showed high toxicity against p53 mutated cell lines (Jurkat, MiaPaca2, DU-145, and MDA-MB-231) as shown in Table 1. Because the activity of cisplatin has been reported to be p53-dependent, new organometallic compounds that activate p53-independent pathways could be useful in the treatment of tumors with alterations in p53, the most frequently mutated gene in human cancer.

Reactivity with Biomolecules—Interactions with DNA.

Because DNA replication is a key event for cell division, it is among critically important targets in cancer chemotherapy. Most cytotoxic platinum drugs form strong covalent bonds with DNA bases. However, a variety of platinum compounds act as DNA intercalators upon coordination to the appropriate ancillary ligands. The more thoroughly studied ruthenium antitumor agents (Chart 1) have displayed differences with respect to their interactions with DNA depending on their structure. Thus, while NAMI-A is known to have fewer and weaker interactions with DNA than cisplatin, indazolium bisindazoletetrachlororuthenate (KP1019) undergoes interactions similar to cisplatin but with a lower intensity in terms of DNA-DNA and DNA-protein cross-links. Organometallic piano-stool ruthenium (II) compounds based on biphenyl rings RM175 interact strongly with DNA binding to guanines and by intercalation. Organometallic ruthenium (II) RAPTA derivatives, characterized by the presence of water-soluble TPA phosphine, exhibit pH-dependent DNA damage: at the pH typical of hypoxic tumor cells DNA was damaged, whereas at the pH characteristic of healthy cells little or no damage was detected. Cyclorinthenated compounds based on pincer C,N ligands (RDC family) displayed a much weaker interaction with plasmid (pBR322) DNA when compared to cisplatin. Complexes of the type [Ru(Cp)(2,2-bipy)(PR$_3$)][CF$_3$SO$_3$] have shown no observable interaction with DNA.

The effect of DNA interactions was evaluated that could, to some extent, contribute to the observed cytotoxicity of compounds 1-4, 8, and 9 and the apoptotic behavior of compounds 2 and 3. The interaction with Calf Thymus DNA (CT DNA) by circular dichroism (CD) and with plasmid pBR322 DNA was followed by electrophoresis in agarose gel. The CD spectral technique is very sensitive to diagnose alterations on the secondary structure of DNA that result from DNA-drug interactions. A typical CD spectrum of CT DNA shows a positive band with a maximum at 275 nm due to base stacking, and a negative band with a minimum at 248 nm due to helipticity, characteristic of the B conformation. Therefore, changes in the CD signals can be assigned to corresponding changes in DNA secondary structure. In addition, it is known that simple groove binding or electrostatic interaction of small molecules cause little or no alteration in any of the CD bands when compared to major perturbations induced by covalent binding or intercalation.

CD spectra of CT DNA incubated with compounds 1-4 at 37° C. and pH=7.30 in Tris/HCl buffer up to molar ratio drug/DNA=0.5 showed no modification of the DNA bands with respect to untreated CT DNA, indicating that drug-DNA interactions, if existing, do not induce any observable perturbation on the DNA secondary structure under our experimental conditions Higher ratios were also tested, although loss of CD signal was observed due to precipitation of the DNA induced by compounds 1-4, most likely because of phosphate charge neutralization by the cationic compounds, which suggests the existence of an electrostatic attraction. DNA condensation or precipitation by neutralization of backbone charges has been previously described for other ionic ruthenium drugs and confirmed by us for compounds 2 and 3 through ICP-MS analysis of metal content in the DNA precipitate. In this experiment, 500 µM concentration DNA solutions were treated with 2 equiv of ruthenium compound 2 and compound 3 for twenty hours at 37° C. to promote DNA precipitation. The samples were then centrifuged, and the resulting pellets were analyzed for DNA and metal concentration. The results show ruthenium content values of 2.60±0.26 mg Ru/mg DNA for compound 2 and 2.43±0.18 mg Ru/mg DNA for compound 3. This high Ru content in DNA precipitate, especially when compared to similar Ru compounds interacting with DNA through covalent interactions, suggests that the key factor promoting the precipitation of DNA is the presence of the ruthenium compound.

Attempts to obtain additional evidence of drug-CT DNA interactions were made by performing thermal denaturation experiments but resulted in cyclometalation of compound 1 and compound 2 and hydrolysis of compound 3 at temperatures above 60° C., as previously discussed, preventing us from obtaining reliable information through this technique.

To gain further insights on the nature of the compound-DNA interactions, gel electrophoresis studies were also performed with the ruthenium(II) complexes 1-4, 8, and 9 on plasmid (pBR322) DNA.

For these experiments, cisplatin, all uncoordinated ligands, and the starting dimeric organometallic ruthenium (II) complex $[Ru(\eta^6\text{-p-cymene})Cl]_2$ were also measured as controls. Plasmid pBR322 presents two main forms, OC (open circular or relaxed) and CCC (covalently closed or supercoiled), which display different electrophoretic mobility. Changes in the electrophoretic mobility of any of the forms upon incubation of the plasmid with a compound are usually interpreted as evidence of interaction. Generally, a drug that induces unwinding of the CCC form will produce a retardation of the electrophoretic mobility, while coiling of the OC form will result in increased mobility. FIG. 5 shows the effect of cisplatin and compounds 1-4, 8, and 9 on DNA pBR322 after incubation at 37° C. for twenty hours in Tris/HCl buffer up to drug/DNA ratio 2.0. As previously reported, cisplatin is able to both increase and decrease the mobility of the OC and the CCC forms, respectively. Interestingly, treatment with increasing amounts of compound 1 and compound 2 induce retardation of the mobility of the CCC form of plasmid DNA, while the rest of the compounds, the neutral ligands, and the Ru starting dimer do not seem to induce any alteration on the mobility of the plasmid.

The results of CD, ICP-MS, and gel electrophoresis taken together suggest that compounds 1-4 undergo only electrostatic interactions with DNA. This conclusion is supported by three main facts: (1) results obtained by CD spectroscopy do not show evidence of CT DNA modifications of secondary structure, suggesting that drug-DNA interactions, if any, are of weak nature, but neither covalent nor intercalation; (2) precipitation of CT DNA is observed in CD experiments at high ratios drug/DNA, and it is further confirmed by ICP-MS analysis of metal content in DNA precipitates, suggesting backbone charge neutralization; and (3) retardation of the plasmid DNA electrophoretic mobility is observed also at high drug/DNA ratios for compound 1 and compound 2, but only when plasmid DNA is incubated with the cationic metal compounds and not with the neutral ligands or neutral ruthenium starting material under the same conditions, which could also be consistent with charge neutralization or DNA precipitation. Loss of migration in electrophoresis experiments has been previously reported as a consequence of DNA precipitation for other cationic ruthenium compounds. The electrophoretic mobility results also suggest that the electrostatic interaction between DNA and compound 1 and compound 2 is of larger magnitude than that experienced by compound 3 and compound 4 because no mobility retardation is observed for the latter compounds up to drug/DNA ratio of 2.0. Further evidence of this could be found in the fact that lower amount of Ru content in DNA is detected for compound 3 when compared to compound 2, according to ICP-MS results.

Without wishing to be bound to any particular theory, the antitumor properties observed for compounds 1-4, 8, and 9 are believed to be due to non-DNA related mechanisms/factors.

Inhibition of Capthesin B

Cathepsin B (cat B) is an abundant and ubiquitously expressed cysteine peptidase of the papain family, which has turned out to be a prognostic marker for several types of cancers. Cathepsin B seems to be involved (along with other cathepsins) in metastasis, angiogenesis, and tumor progression. It has been proposed that cat B may be a possible therapeutic target for the control of tumor progression. RAPTA Ru compounds which inhibit cat B with $IC_{50}$ in the low micromolar range can reduce the mass and number of metastases in vivo. The inhibition of Cat B by compound 2 was therefore studied. Compound 2 does not inhibit the enzymatic activity of cat B at concentrations up to 100 μM, indicating that this protease may not be a target for this type of arene-ruthenium (II) derivatives.

Interactions with HAS Human serum albumin (HSA) is the most abundant carrier protein in plasma and is able to bind a variety of substrates including metal cations, hormones, and most therapeutic drugs. The distribution, the free concentration, and the metabolism of various drugs can be significantly altered as a result of their binding to the protein. HSA possesses three fluorophores, namely tryptophan (Trp), tyrosine (Tyr), and phenylalanine (Phe) residues, with Trp214 being the major contributor to the intrinsic fluorescence of HSA. This Trp fluorescence is sensitive to the environment and binding of substrates, as well as changes in conformation that can result in quenching (either dynamic or static).

Figure 7A:
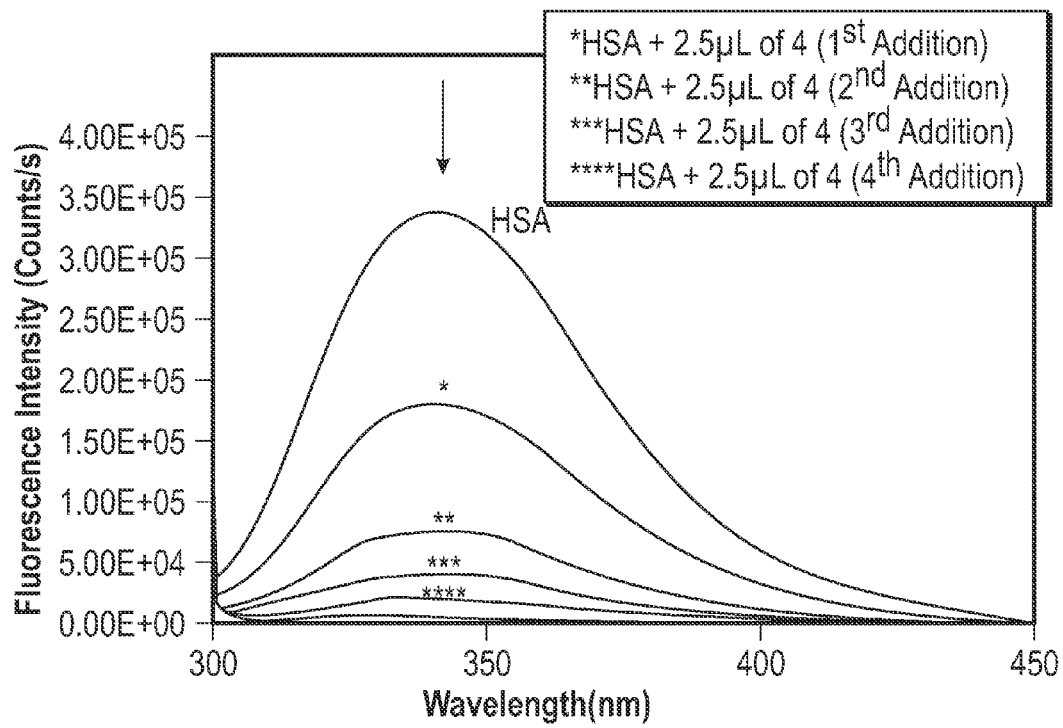
FIG. 7A is a graph of a fluorescence titration curve of HAS with compound 4 wherein 10 aliquots of 2.5 μL of compound 4 (8 mM in DMSO) was added successively to a solution of HSA (10 μM in phosphate buffer, pH=7.4) and the arrow indicates the increase of quencher concentration. (10-100 mM)
Figure 7B:
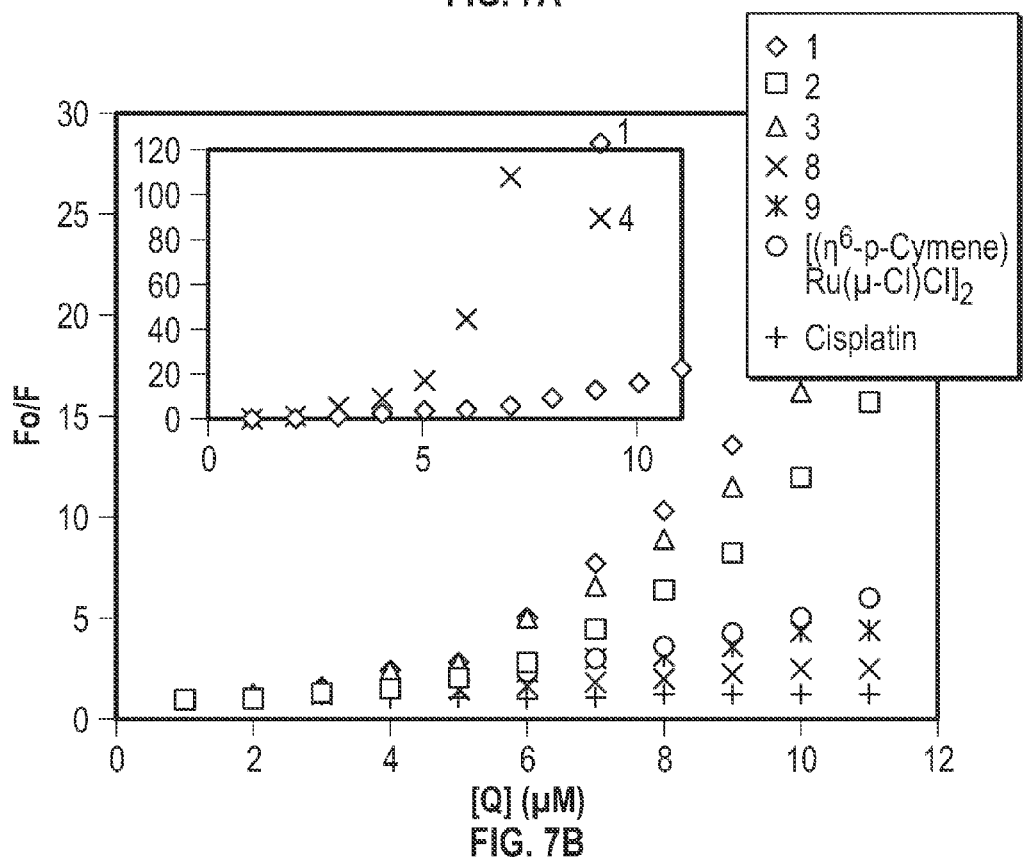
FIG. 7B is a Stern-Volmer plot for HAS fluorescence quenching observed with compounds 1-4, 8, 9 Ru-dimer and cisplatin.

Thus, the fluorescence spectra of HSA in the presence of increasing amounts of the compounds 1-4, 8, 9, and cisplatin were recorded in the 300-450 nm range upon excitation of the tryptophan residue at 295 nm. The compounds caused a concentration dependent quenching of fluorescence without changing the emission maximum or the shape of the peak. All these data indicate an interaction of the compounds with HSA. The fluorescence data was analyzed by the Stern-Volmer equation. While a linear Stern-Volmer plot is indicative of a single quenching mechanism, either dynamic or static, the positive deviation observed in the plots of F0/F versus [Q] of compounds 1-4 (FIG. 7A and FIG. 7B) suggests the presence of different binding sites in the protein with different binding affinities. A similar behavior was observed in the case of coordination iminophosphorane complexes of d8 metals for which a concentration-dependent fluorescence quenching was reported. On the other hand, the Stern-Volmer plot for compound 8 and compound 9 shows a linear relationship, suggesting the existence of a single quenching mechanism, most likely dynamic, and a single binding affinity. The Stern-Volmer constants for compound 8 and compound 9 are $1.81 \times 10^4$ and $3.85 \times 10^4$ $M^{-1}$, respectively.

In general, higher quenching by the iminophosphorane complexes was observed compared to that of cisplatin under the chosen conditions, most likely due to the faster reactivity of our compounds with HSA, as compared to cisplatin.

Evaluation of the Lethal and Maximum Tolerated Doses

Compound 2 was evaluated in C57/Black6 mice. The lethal dose was determined to be 30 mg/kg/day. No biological samples were collected from those mice. The MTD was determined to be 10 mg/kg/day, at which the mice showed no visible signs of distress over the 7 days course of treatment.

Mice lost weight during the trial in a dose dependent manner where mice treated with 5, 10, or 20 mg/kg/day lost 15%, 19%, or 37% body weight, respectively, while vehicle treated mice gained 3% body weight over the 7 days of treatment. Mice treated with 20 mg/kg/day were euthanized on day 6 of the trial as they had lost too much body weight and looked in distress.

Twenty-four hours after the last dose, all the mice used in the MTD study were euthanized and blood plasma, liver, spleen, and kidneys were collected and used for histological analysis. Necropsy and histology indicate that mice treated at 20 mg/kg/day had discolored livers and atrophied spleens; at 10 mg/kg/day, much less atrophy and minor discoloration was observed, while in mice treated at 5 mg/kg/day, there was no detectable liver discoloration and no observable change in spleen size.

The dose of 5 mg/kg/every other day was chosen to conduct the subsequent in vivo trial with compound 2.

Effects of Compound 2 in MDA-MB-231 Mouse Xenografts

Twelve female NOD.CB17-Prkdc SCID/J (nonobese diabetic-severe combined immunodeficiency) were selected for the in vivo trial. The mice were inoculated with MDA-MB-231 cells and treated when the tumors were palpable (about 5-6 mm diameter). Each six MDA-MB-231-transplanted animals received compound 2 (5 mg/kg/every other day) or vehicle (0.9% NaCl) intraperitoneally (ip). To palliate the weight loss observed in the MTD study, all the mice used in this trial were fed a 46% fat-adjusted diet (Harlan Teklad, Madison, Wis.) plus HydroGel (Harlan Teklad, Madison, Wis.) and received subcutaneous injection of 100 µL normal saline on the off-treatment day.

Figure 8:
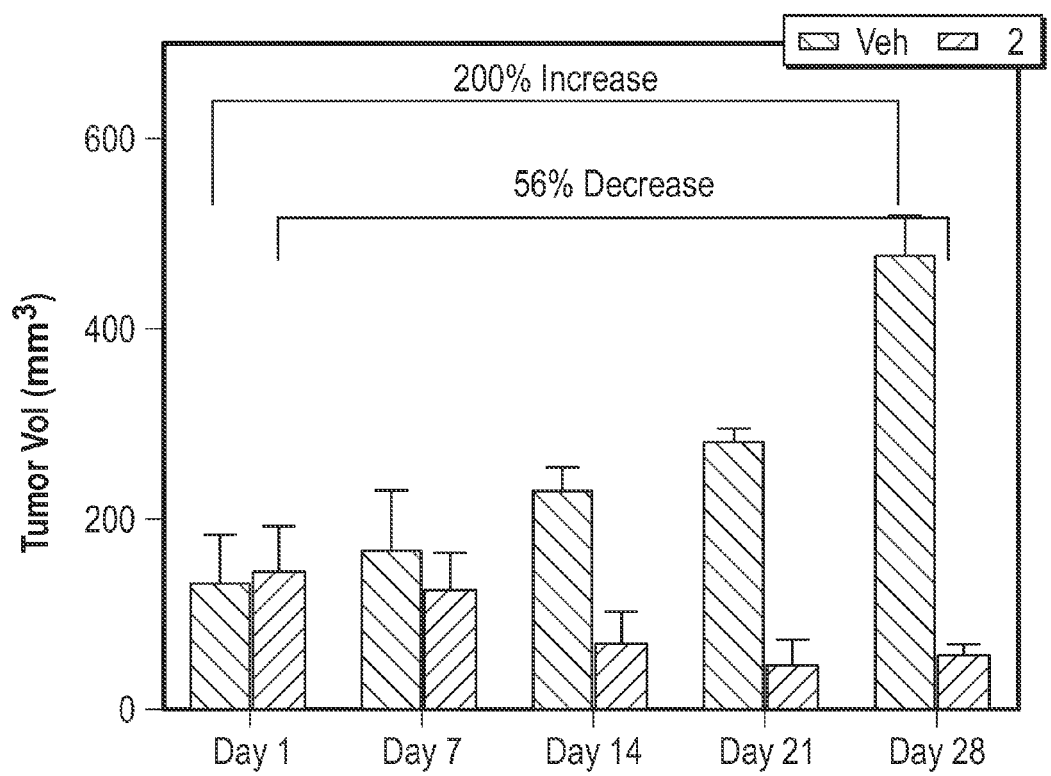
FIG. 8 is a graph showing percent of reduction of tumor burden in a cohort of 12 female NOD.CB17-Prkdc scid/J mice inoculated subcutaneously with $5 \times 10^6$ MDA-MB-231 cells.

In the group treated with compound 2 (see Table 2 and FIG. 8) a significant decrease in tumor size (shrinkage) of 56% was observed compared to the starting volume between day 1 and day 28 of treatment (after a total of 14 doses). The treatment was started when tumors were palpable (5-6 mm diameter). Six mice were treated with compound 2, six were treated with the vehicle 100 µL of normal saline (0.9% NaCl). Compound 2 was administered in the amount of 5 mg/kg/every other day. In the control vehicle treated group, a 200% increase in tumor volume between day 1 and day 28 of treatment was observed. One compound 2-treated mouse was removed from the trial because it was not feeding itself and showed other signs of distress, none of which were observed in the other mice on trial. There was no significant weight loss in mice treated with 5 mg/kg/every other day. Mice treated with compound 2 gained an average weight of 2.88%, while untreated mice gained an average of 18.67% weight (all groups were fed a 46% fat-adjusted diet).

TABLE 2

Effects of 2 on the Tumor Growth of MDA-MB-231 Mammary Carcinoma in NOD.CB17-Prkdc scid/J Mice

| Treatment group | Primary tumor (mm³) |
| --- | --- |
| Controls | 473.47 ± 45.44 |
| Compound 2 (5/mg/kg/eod$^a$ × 14) | 59.58 ± 8.66 | eod-every other day.
Tumor measured on day 28, after the 14$^{th}$ dose

The results clearly indicate that compound 2 is extremely efficient in vivo because it not only inhibits tumor growth but also results in the decrease in the size of the tumors by 56%. It is interesting to compare these results with those obtained with other arene-ruthenium (II) derivatives. Compound RM175 was reported to have a final primary tumor growth inhibition of 30% at a dose of 7.5 mg/kg/day in an in vivo trial for breast cancer in mice, while the compounds RAPTA-C reduced the growth of lung metastases in CBA mice bearing the MCa mammary carcinoma in the absence of a corresponding action at the site of primary tumor growth. More recently, a ruthenium-arene complex with a perfluoroalkyl-containing amine ligand demonstrated a 90% reduction in the tumor growth in a xenografted ovarian carcinoma tumor (A2780) grown in a chorioallantoic membrane (CAM) assay of chicken embryo. As stated above, compound 2 is able to decrease tumor size.

Figure 9:
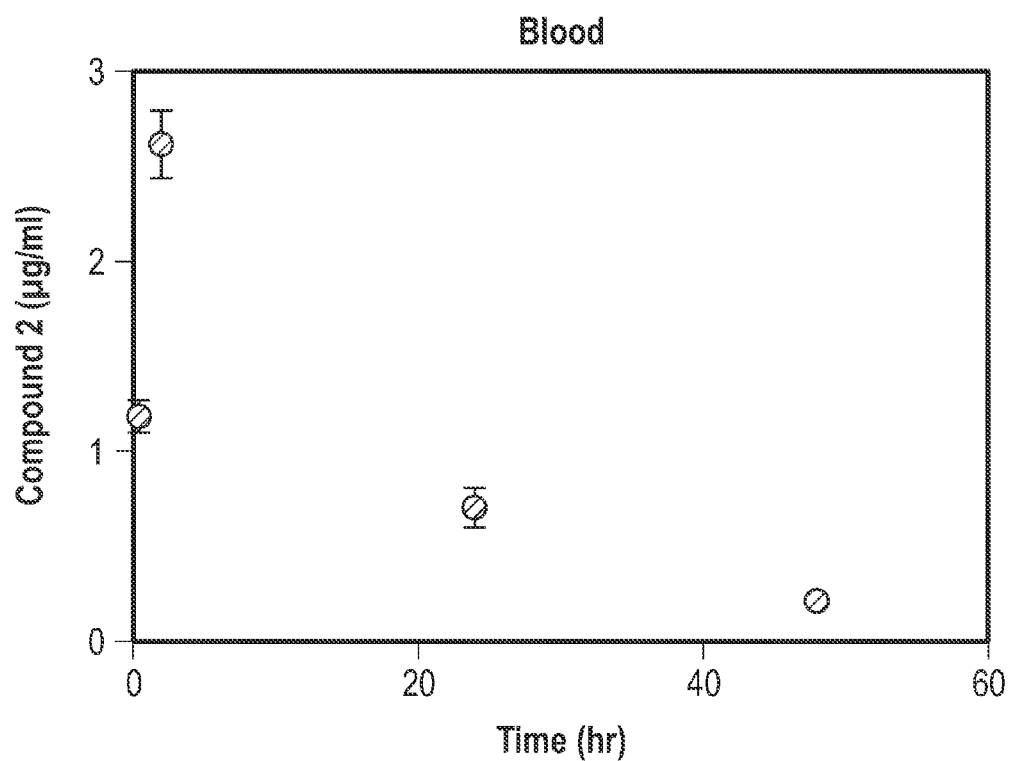
FIG. 9 is a graph showing concentration of compound 2 (ruthenium content) in plasma at various intervals after the first dose.

The pharmacokinetic profile of compound 2 in the NOD.CB17-Prkdc scid/J mice used for the in vivo study (FIG. 9) is summarized in Table 3. Ruthenium content was determined using inductively coupled plasma-mass spectrometry (ICP-MS). Compound 2 was absorbed quickly into plasma ($t_{1/2\ abs}$=0.5 h), and the peak plasma concentration was reached within two hours of dosing. The drug was eliminated slowly from the blood compartment with an elimination half-life ($t_{1/2e}$) greater than twelve hours.

TABLE 3

Pharmacokinetic Parameters of Compound 2 after First Injection in NOD.CB17-Prkdc SCID/J Mice

| Pharmacokinetic parameters | Values |
| --- | --- |
| $K_{abs}$ (h$^{-1}$) | 1.39 |
| $K_e$ (h$^{-1}$) | 0.055 |
| $t_{1/2e}$ (h) | 12.67 |
| $t_{1/2abs}$ (h) | 0.50 |
| $t_{max}$ (h) | 2.00 |
| $C_{max}$ (µg/mL) | 2.62 |
| AUC$_{total}$ (µg · h/mL) | 54.47 |
| $V_{app}$ (mL) | 33.57 |
| CL$_{app}$ (mL/h) | 1.84 |

During determination of total area under the concentration-time curve (AUC total), only 7% of the AUC was extrapolated from the last time point, suggesting a high confidence in the AUC, Vapp, and apparent clearance (CLapp) determination. Blood concentration, at six hours after the last dose of compound 2, was 4.2±1.3 µg/mL, which is higher (P<0.1) than the $C_{max}$ after the first dose. This suggests an accumulation of compound 2 after each dose. While it is difficult to make comparisons with other ruthenium compounds for which a PK analysis has been performed (e.g., RAPTA-C,16 NAMI-A,76 and KP101910) due to the different structures, oxidation states and the amounts employed in these studies, there are some differences that can be pointed out. The $V_d$ (volume of distribution) of compound 2 when compared to that of more structurally related arene-ruthenium (II) RAPTA-C derivative is smaller, which may be due to a higher water solubility of compound 2 or the possibility that it binds strongly to plasma proteins. Indeed, compound 2 binds faster to HSA than cisplatin.

Figure 10:
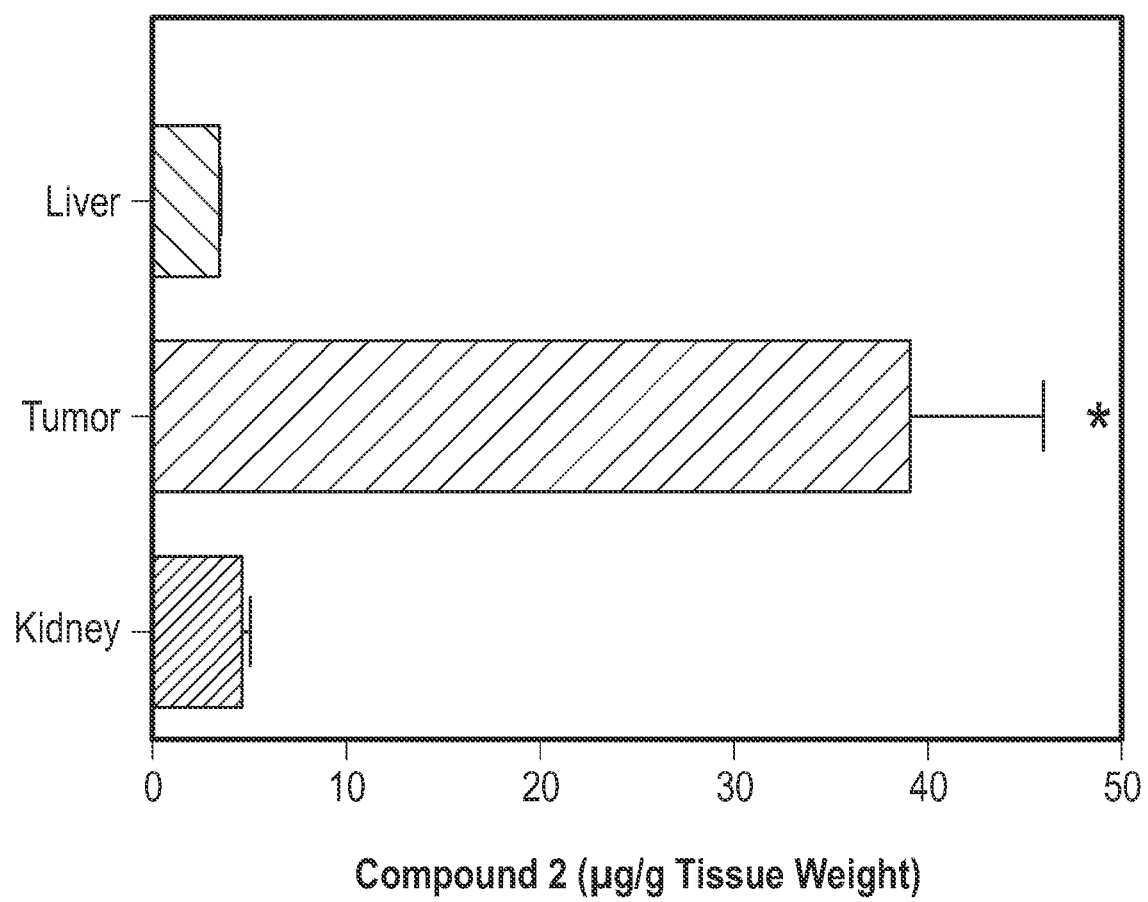
FIG. 10 is a graph depicting compound 2 ruthenium content in tissues at the end of efficacy study wherein data represents mean±SD N=3 and * indicates P<0.05.

At the end of the study, ruthenium content in liver, kidney, and tumor was determined (FIG. 10). The level of compound 2 in liver and kidney was less than 5 µg/g tissue weight, while the tumor concentration was about 40 µg/g. The high level in tumor suggests enhanced tumor accumulation of compound 2, which may explain the high efficacy observed for this compound in the in vivo studies.

The potential of a highly water-soluble ruthenium-arene-iminophosphorane compound 2 has been demonstrated as an anticancer agent. This compound is active against a number of cisplatin resistant cell lines while being less toxic on human renal proximal tubular cell lines. Initial mechanistic studies indicate that the cell death type for compound 2 is mainly through canonical or caspase-dependent apoptosis. In addition, cell death seems not to be dependent on p53. The interaction of compound 2 with DNA is weak and electrostatic in nature. Compound 2 does not inhibit protease cathepsin B in concentrations of 100 µM or lower. The efficacy of compound 2 in vivo has been demonstrated on xenografted breast carcinoma MDA-MB-231 tumors grown on NOD.CB17-Prkdc scid/J mice. An impressive tumor reduction (shrinkage) of 56% was observed after 28 days treatment (14 doses of 5 mg/kg every other day) with low systemic toxicity. Pharmacokinetic studies showed a quick absorption of 2 in plasma with an elimination half-life of 12.67 h (similar to that reported for other ruthenium derivatives). Importantly, compound 2 accumulated preferentially in the breast tumor tissues when compared to kidney and liver, which may explain its high efficacy in vivo. The simple, cheap, and accessible synthesis of compound 2, its high water-solubility, and its encouraging preliminary biological activity in vitro and in vivo makes it therefore a good candidate for further evaluation as a potential chemotherapeutic agent.

While the invention has been described with reference to certain embodiments, it will be understood by those skilled in the art that various changes may be made and equivalents may be substituted for elements thereof to adapt to particular situations without departing from the scope of the disclosure. Therefore, it is intended that the claims not be limited to the particular embodiments disclosed, but that the claims will include all embodiments falling within the scope and spirit of the appended claims.

EXPERIMENTAL

All manipulations involving air-free syntheses were performed using standard Schlenk-line techniques under a nitrogen atmosphere or a glove-box MBraun MOD System. Solvents were purified by use of a PureSolv purification unit from Innovative Technology, Inc. Compounds [PhCH$_2$Mn(CO)$_5$], [$\eta^6$-p-cymene)Ru(µ-Cl)Cl]$_2$, [Hg(2-C$_6$H$_4$C(O)N=PPh$_3$)Cl], and IM ligands Ph$_3$P=N—CO-2-N—C$_5$H$_4$, Ph$_3$P=N-8-C$_9$H$_6$N, [Cp-P(Ph$_2$)=N—CH$_2$-2-NC$_5$H$_4$]Fe(Cp)], and Ph$_3$P=N—CO-2-C$_6$H$_4$ were prepared by reported methods. The purity of the compounds, based on elemental analysis, is ≥99.5%. Elemental analyses were performed by Atlantic Microlab Inc. NMR spectra were recorded in a Bruker AV400 ($^1$H NMR at 400 MHz, $^{13}$C NMR at 100.6 MHz, $^{31}$P NMR at 161.9 MHz). Chemical shifts (δ) are given in ppm using CDCl$_3$ or d$^6$-DMSO as solvent, unless otherwise stated. $^1$H and $^{13}$C chemical shifts were measured relative to solvent peaks considering TMS=0 ppm; $^{31}$P {$^1$H} was externally referenced to H$_3$PO$_4$ (85%). Infrared spectra (4000-250 cm$^{-1}$) were recorded on a Nicolet 6700 FT-IR spectrophotometer from nujol mulls between polyethylene sheets. Mass spectra (electrospray ionization, ESI) were performed on an Agilent Analyzer, a Bruker Analyzer, or a Waters Q-Tof Ultima analyzer. Conductivity was measured in an OAKTON pH/conductivity meter in CH$_3$CN solutions ($10^{-3}$M). X-ray collection was performed at room temperature on a Kappa CCD diffractometer using graphite monochromated Mo—Kα radiation (λ=0.71073 Å). Electrophoresis experiments were carried out in a Bio-Rad Mini sub-cell GT horizontal electrophoresis system connected to a Bio-Rad Power Pac 300 power supply. Photographs of the gels were taken with an Alpha Innotech FluorChem 8900 camera. Fluorescence intensity measurements were carried out on a PTI QM-4/206 SE Spectrofluorometer (PTI, Birmingham, N.J.) with right angle detection of fluorescence using a 1 cm path length quartz cuvette. Circular dichroism spectra were recorded using a Chirascan CD Spectrometer equipped with a thermostated cuvette holder. The inhibition of Capthesin B experiments were performed by Reaction Biology Corporation.

Synthesis

[($\eta^6$-p-cymene)Ru{(Ph$_3$P=N—CO-2-N—C$_5$H$_4$)-κ-N, O}Cl](PF$_6$): [($\eta^6$-p-cymene)Ru(µ-Cl)Cl]$_2$ (0.15 g, 0.25 mmol) was dissolved in MeOH (15 mL) and Ph$_3$P=N(CO)(C$_5$H$_5$-2-N) (0.19 g, 0.5 mmol) was added. To the resulting mixture KPF$_6$ (0.10 g, 0.55 mmol) was added. The mixture was stirred for 4 h. The suspension was then filtered and washed 3 times with Et$_2$O (10 mL). The solution was then concentrated and the precipitate was collected by filtration and dried in vacuo. Yield: 0.36 g (90%). Anal. Calc. for C$_{34}$H$_{33}$N$_2$OP$_2$F$_6$ClRu (798.07): C, 51.17; H, 4.17; N, 3.51. Found: C, 50.95; H, 4.20; N, 3.56%. ESI-MS: m/z: 653.10 (100%, [M−PF$_6$]$^+$, calc. 653.11). $^{31}$P {$^1$H} NMR (CDCl$_3$): δ 25.72 (s), −148.26 to −140.19 (septet, PF$_6$), (d$_6$-DMSO): 24.27 (s), −152.87 to −130.98 (septet, PF$_6$ $^1$H NMR (CDCl$_3$): δ 1.10 (6H, dd, J=6.9, 18.9 Hz, CH$_3$, $\eta^6$-p-cymene), 1.69 (3H, s, CH$_3$, $\eta^6$-p-cymene), 1.65 (3H, s, CH$_3$, $\eta^6$-p-cymene), 2.30 (1H, m, CH, $\eta^6$-p-cymene), 5.48-5.59 (4H, m, CH, $\eta^6$-p-cymene), 7.64-7.78 (16H, m, H$_5$, H$_m$+H$_o$+H$_p$), 8.03 (1H, d, J=7.7 Hz, H$_4$, C$_5$H$_4$N), 8.35 (1H, d, J=7.5 Hz, H$_3$, C$_5$H$_4$N), 9.21 (1H, d, J=5.3 Hz, H$_6$, C$_5$H$_4$N); $^{13}$C {$^1$H} (CDCl$_3$): δ 18.10 (s, CH$_3$, $\eta^6$-p-cymene), 21.87 (s, CH$_3$, $\eta^6$-p-cymene), 22.18 (s, CH$_3$, $\eta^6$-p-cymene), 30.79 (s, CH, $\eta^6$-p-cymene), 81.00 (s, CH, $\eta^6$-p-cymene), 82.09 (d, CH, J=8.3 Hz, $\eta^6$-p-cymene), 82.41 (s, CH, $\eta^6$-p-cymene), 83.92 (s, C, $\eta^6$-p-cymene), 124.5 (s, C$_2$, $\eta^6$-p-cymene), 125.5 (d, C$_{ipso}$, J=100.4 Hz), 127.7 (s, C$_3$, C$_5$H$_4$N), 129.5 (d, C$_m$, J=13.0 Hz), 129.8 (s, C$_5$, C$_5$H$_4$N), 133.2 (d, C$_o$, J=10.4 Hz), 133.8 (s, C$_p$), 139.3 (s, C$_4$, C$_5$H$_4$N), 153.7 (s, C$_6$) ppm. The signal due to C$_2$ (C$_5$H$_4$N) and C=O was not observed. IR (cm$^{-1}$): ν 524 (Ru—N), 834 (v br, PF$_6^-$), 1116 (N=P), 1540 (C=O). Conductivity (acetone): 125.5 µS/cm (1:1 electrolyte).

[($\eta^6$-p-cymene)Ru{(Ph$_3$P=N—CO-2-N—C$_5$H$_4$)-κ-N, O}Cl]Cl: [($\eta^6$-p-cymene)Ru(µ-Cl)Cl]$_2$ (0.15 g, 0.25 mmol) and Ph$_3$P=N(CO)(C$_5$H$_5$-2-N) (0.19 g, 0.5 mmol) were stirred in acetone (20 mL) for 3 h. The brown solution was concentrated and 30 mL of Et$_2$O added dropwise. The orange solid that formed was collected by filtration and dried in vacuo. Yield: 0.33 g (94%). Anal. Calc. for C$_{34}$H$_{33}$N$_2$OPCl$_2$Ru.2H$_2$O (724.62): C, 56.36; H, 5.15; N, 3.87. Found: C, 56.41; H, 4.99; N, 3.87%. ESI-MS: m/z: 653.1 (100%, [M−Cl]$^+$, calc. 653.01), 618.1 (100%, [M−2Cl]$^{2+}$, calc. 618.1), 519.0 (100%, [M-p-cymene-Cl]$^+$, calc. 519.0). $^{31}$P {$^1$H} NMR (CDCl$_3$): δ 25.18 (s), (d$_6$-DMSO): 28.99 (s); $^1$H NMR (CDCl$_3$): δ 1.00 (6H, dd, J=7.0, 24.8, Hz CH$_3$, $\eta^6$-p-cymene), 2.01 (3H, s, CH$_3$, $\eta^6$-p-cymene), 2.25 (1H, m, CH, $\eta^6$-p-cymene), 5.51-5.71 (4H, m, CH, $\eta^6$-p-cymene), 7.57 (6H, m, H$_{meta}$), 7.68 (9H, m, H$_{ortho}$+H$_{para}$), 7.87 (1H, d, J=6.0 Hz, H$_5$, C$_5$H$_4$N), 8.03 (1H, d, J=7.7 Hz, H$_4$, C$_5$H$_4$N), 8.32 (1H, d, J=7.4 Hz, H$_3$, C$_5$H$_4$N), 9.62 (1H, d, J=5.0 Hz, H$_6$, C$_5$H$_4$N); $^{13}$C {$^1$H} (CDCl$_3$): δ 18.47 (s, CH$_3$, $\eta^6$-p-cymene), 21.82 (s, CH$_3$, $\eta^6$-p-cymene), 22.39 (s, CH$_3$, $\eta^6$-p-cymene), 30.75 (s, CH, $\eta^6$-p-cymene), 81.20 (s, CH, $\eta^6$-p-cymene), 82.60 (d, CH, J=8.3 Hz, $\eta^6$-p-cymene), 83.65 (s, CH, $\eta^6$-p-cymene), 97.87 (s, C, $\eta^6$-p-cymene), 102.5 (s, C, $\eta^6$-p-cymene), 125.6 (d, C$_{ipso}$, J=101.2 Hz), 127.2 (s, C$_3$, C$_5$H$_4$N), 129.5 (d, C$_m$, J=12.8 Hz), 130.3 (s, $C_5$, $C_5H_4N$), 133.3 (d, $C_o$, J=10.2 Hz), 133.9 (s, $C_p$), 139.0 (s, $C_4$, $C_5H_4N$), 151.6 (d, $C_2$, J=24.0 Hz), 156.3 (s, $C_6$), 176.8 (d, C=O, J=24.14 Hz) ppm. IR (cm$^{-1}$): ν 527 (Ru—N), 1114 (N=P), 1535 (C=O). Conductivity (acetone): 124.20 μS/cm (1:1 electrolyte). Solubility: 145.3 mM or 100 mg/mL ($H_2O$). pH (5×10$^{-5}$M in $H_2O$): 5.76.

[($η^6$-p-cymene)Ru{($Ph_3P$=N-8-$C_9H_6N$)-κ-N,N}Cl]Cl: [($η^6$-p-cymene)Ru(μ-Cl)Cl]$_2$ (0.092 g, 0.15 mmol) was dissolved in $CH_2Cl_2$ (15 mL) and $Ph_3P$=N-8-$C_9H_6N$ (0.12 g, 0.3 mmol) was added. The mixture was stirred for 3 h. The solution was concentrated to 2 mL and 20 mL of $Et_2O$ added to precipitate an orange solid, which was filtered and dried in vacuo. Yield: 0.18 g (84%). Anal. Calc. for $C_{37}H_{35}N_2PCl_2Ru.2.5H_2O$ (755.68): C, 58.81; H, 5.34; N, 3.71. Found: C, 58.95; H, 4.81; N, 3.82%. ESI-MS: m/z: 675.13 (100%, [M−Cl]$^+$, calc. 675.13), 540.0 (100%, [M-p-cymene-Cl]$^+$, calc. 541.02). $^{31}$P {$^1$H} NMR (CDCl$_3$): δ 37.68 (s), (d$_6$-DMSO): 37.84 (s); $^1$H NMR (CDCl$_3$): δ 0.73 (3H, d, J=6.7 Hz, $CH_3$, $η^6$-p-cymene), 1.01 (3H, d, J=6.6 Hz, $CH_3$, $η^6$-p-cymene), 1.98 (3H, s, $CH_3$, $η^6$-p-cymene), 2.44 (2H, m, CH, $η^6$-p-cymene), 5.43 (2H, s, CH, $η^6$-p-cymene), 5.72 (2H, s, CH, $η^6$-p-cymene), 6.40 (1H, d, J=8.0 Hz, $H_7$, $C_9H_6N$), 6.91 (1H, d, J=8.1 Hz, $H_7$, $C_9H_6N$), 7.15 (1H, d, J=8.1 Hz, $H_7$, $C_9H_6N$), 7.66 (9H, m, $H_m$+$H_p$), 7.68 (1H, s, $H_3$, $C_9H_6N$), 8.00 (6H, m, $H_o$), 8.21 (1H, d, J=8.4 Hz, $H_4$, $C_9H_6N$), 8.21 (1H, s, $H_2$, $C_9H_6N$). $^{13}$C {$^1$H} (CDCl$_3$): δ 19.20 (s, $CH_3$, $η^6$-p-cymene), 21.02 (s, $CH_3$, $η^6$-p-cymene), 22.96 (s, $CH_3$, $η^6$-p-cymene), 31.62 (s, CH, $η^6$-p-cymene), 118.4 (s, $C_5$, $η^6$-p-cymene), 121.7 (d, $C_7$, J=10.3 Hz, $η^6$-p-cymene), 124.6 (s, $C_3$, $η^6$-p-cymene), 125.8 (s, $C_6$), 129.4 (s, $C_8$), 129.6 (d, $C_m$, J=12.7 Hz), 130.0 (s, $C_{ipso}$), 134.1 (s, $C_p$), 134.9 (d, $C_o$, J=9.8 Hz), 138.4 (d, $C_4$), 144.7 (s, $C_9H_6N$), 144.9 (s, $C_9H_6N$), 149.2 (s, C=NP) ppm. Signals due to the quaternary C atoms were not observed. IR (cm$^{-1}$): ν 519 (Ru—N), 1268 (N=P). Conductivity (acetone): 125.60 μS/cm (1:1 electrolyte). Solubility: 112.6 mM or 80 mg/mL ($H_2O$).

[($η^6$-p-cymene)Ru([{Cp—P(Ph$_2$)=N—CH$_2$-2-NC$_5H_4$}Fe(Cp)]-κ-N,N)Cl]Cl: To a solution of [($η^6$-p-cymene)Ru(μ-Cl)Cl]$_2$ (0.16 g, 0.26 mmol) in $CH_2Cl_2$ (10 mL), [{Cp—P(Ph$_2$)=N—CH$_2$-2-NC$_5H_4$}Fe(Cp)] (0.25 g, 0.52 mmol) in $CH_2C_2$ (10 mL) was added and stirred for 40 min. The solvent removed to dryness under reduced pressure. The solid was dissolved in $CH_2Cl_2$ and 25 mL of $Et_2O$ were added. The solid formed was then filtered and dried in vacuo. Yield: 0.30 g (81%). Anal. Calc. for $C_{38}H_{39}N_2FePCl_2Ru.3.5H_2O$ (845.59): C, 53.98; H, 5.48; N, 3.31. Found: C, 54.02; H, 5.30; N, 3.47%. ESI-MS: m/z: 747.0 (100%, [M−Cl]$^+$, calc. 747.1), 613.0 (100%, [M-p-cymene-Cl], calc. 612.98). $^{31}$P {$^1$H} NMR (CDCl$_3$): δ 46.40 (s), (d$_6$-DMSO): 45.99 (s), (D$_2$O): 46.95 (s); $^1$H NMR (CDCl$_3$): δ 0.99 (3H, d, J=5.4 Hz, $CH_3$, $η^6$-p-cymene), 1.23 (3H, m, $CH_3$+$CH_2$, $η^6$-p-cymene, $NCH_2C$), 2.03 (3H, s, $CH_3$, $η^6$-p-cymene), 3.51 (1H, m, CH, $η^6$-p-cymene), 3.98 (5H, s, $C_5H_5$), 4.42-4.78 (6H, m, $CH_2$+$C_5H_4$), 4.79 (2H, m, Cp), 5.17-5.62 (4H, m, CH, $η^6$-p-cymene), 7.45-7.68 (10H, m, $H_{m+o+p}$), 7.83 (1H, d, J=7.4 Hz, $H_5$, $C_5H_4N$), 7.98 (2H, d, J=7.7 Hz, $H_{3+4}$, $C_5H_4N$), 9.09 (1H, d, J=4.7 Hz, $H_6$, $C_5H_4N$); $^{13}$C {$^1$H} (CDCl$_3$): δ 18.91 (s, $CH_3$, $η^6$-p-cymene), 21.99 (d, $CH_3$+$CH_3$, $η^6$-p-cymene), 23.25 (s, $CH_3$, $η^6$-p-cymene), 31.30 (s, CH, $η^6$-p-cymene), 70.55 (s, Cp), 72.24 (d, J=9.9 Hz, Cp), 73.73 (d, J=9.9 Hz, Cp), 75.03 (m, Cp), 83.29 (d, CH, J=14.4 Hz, $η^6$-p-cymene), 85.98 (d, 2CH, J=8.3 Hz, $η^6$-p-cymene), 87.09 (s, CH, $η^6$-p-cymene), 99.99 (s, C, $η^6$-p-cymene), 103.8 (s, C, $η^6$-p-cymene), 124.9 (s, Ph), 128.4-128.8 (m, Ph), 130.2 (s, $C_{ipso}$), 133.0-133.3 (s, Ph), 133.9-134.0 (d, $C_3$+$C_4$, J=10.1 Hz, $C_5H_4N$), 138.8 (s, $C_4$, $C_5H_4N$), 155.1 (s, $C_2$, $C_5H_4N$), 164.1 (s, $C_6$) ppm. IR (cm$^{-1}$): ν 488 (Ru—N), 1116 (N=P). Conductivity (MeCN): 130.37 μS/cm (1:1 electrolyte). Solubility: 89.5 mM or 70 mg/mL ($H_2O$).

[PTA=N—C(O)-2-$C_6H_5$]: PTA (0.34 g, 2.18 mmol) and benzamide (0.264 g, 2.18 mmol) were placed in a Schlenk flask under nitrogen. Dry, degassed THF (10 mL) was added and to this solution, $^t$BuDAD (N,N-bis(tert-butyl) 1,4-diazabutadiene) (0.503 g, 2.18 mmol) in dry and degassed THF (4 mL) was added dropwise at 0° C. The reaction was left stirring at RT for 2.5 h. After this period, the solvent was removed to dryness under reduced pressure. The white residue was washed three times with $Et_2O$ (15 mL) giving a white solid that was filtered and dried in vacuo. Yield: 0.53 g (88%). Anal. Calc. for $C_{13}H_{17}N_4OP$ (276.11): C, 56.52; H, 6.20; N, 20.28. Found: C, 55.55; H, 6.16; N, 20.69%. ESI-MS: m/z: 277.12.0 (99.6%, [M]$^+$, calc. 276.11). $^{31}$P {$^1$H} NMR (CDCl$_3$): δ −30.8 (s); $^1$H NMR (CDCl$_3$): δ 4.32-4.63 (12H, m, PTA), 7.38 (2H, t, J=7.6 Hz, $H_3$+$H_5$, $C_6H_5$), 7.44 (1H, t, J=7.1 Hz, $H_4$, $C_6H_5$), 8.07 (2H, d, J=7.5 Hz, $H_2$+$H_6$, $C_6H_5$); $^{13}$C {$^1$H} (CDCl$_3$): δ 55.10 (d, J=47.2 Hz, PTA), 72.60 (d, J=8.9 Hz, PTA), 128.08 (s, $C_3$+$C_5$, $C_6H_4$), 129.21 (s, $C_2$+$C_6$, $C_6H_4$), 131.47 (s, $C_4$), 136.74 (d, J=17.7 Hz, $C_1$), 179.28 (s, J=9.6 Hz, C=O). Conductivity (acetone): 2.08 μS/cm (neutral).

[(CO)$_4$Mn(2-$C_6H_4$C(O)N=PTA)]: $PhCH_2$Mn(CO)$_5$ (0.43 g, 1.5 mmol) and PTA=NC(O)Ph (5) (0.41 g, 1.5 mmol) were refluxed in n-hexane (45 mL) for 4 h. The hot solution was filtered and the yellow filtrate reduced in volume until signs of crystallization became evident. Storage at −20° C. gave yellow crystals of (CO)$_4$Mn(2-$C_6H_4$C(O)N=PTA). Yield: 0.59 g (90%). Anal. Calc. for $C_{17}H_{16}N_4O_4$PMn (442.02): C, 46.07; H, 3.65; N, 12.67. Found: C, 45.69; H, 3.56; N, 12.72%. ESI-MS: m/z: 443.03 (100%, [M], calc. 443.03), 415.04 (100%, [M−CO], calc. 415.04), 386.01 (100%, [M−2CO], calc. 387.04), 331.05 (100%, [M−4CO], calc. 331.05). $^{31}$P {$^1$H} NMR (CDCl$_3$): δ −15.27 (s); $^1$H NMR (CDCl$_3$): δ 4.32-4.58 (12H, m, PTA), 7.16 (1H, t, J=7.5, 14.8 Hz, $H_4$, $C_6H_4$), 7.38 (1H, t, J=7.5, 14.5 Hz, $H_3$, $C_6H_4$), 7.68 (1H, d, J=7.6 Hz, $H_2$, $C_6H_4$), 7.93 (1H, d, J=7.4 Hz, $H_5$, $C_6H_4$); $^{13}$C {$^1$H} (CDCl$_3$): δ 53.30 (d, J=43.3 Hz, PTA) ppm. 72.54 (d, J=9.8 Hz, PTA), 124.02 (s, $C_4$, $C_6H_4$), 128.60 (s, $C_2$, $C_6H_4$), 132.55 (s, $C_3$, $C_6H_4$), 139.93 (s, $C_1$), 141.25 (s, $C_5$, $C_6H_4$), 171.36 (s, C=O), 185.71 (s, C=O), 213.66 (s, C=O), 215.97 (s, C=O) ppm. Conductivity (acetone): 1.11 μS/cm (neutral).

[Hg(2-$C_6H_4$C(O)N=PTA)Cl]: (CO)$_4$Mn(2-$C_6H_4$C(O)N=PTA) (0.44 g, 1.0 mmol) and HgCl$_2$ (0.54 g, 2.0 mmol) were refluxed in methanol (55 mL) for 5 h during which time the solution turned yellow and a white solid formed. The mixture was cooled in an ice-water bath and subsequently filtered. The white solid formed was washed well with cold methanol. The solid was redissolved in $CH_2Cl_2$ (<200 mL) and filtered through celite. The resulting clear solution was reduced in volume (<3 mL) and $Et_2O$ was added dropwise until the solution became cloudy. Storage at −20° C. gave white crystals of 7, which were filtered off, dried and used without further purification. Yield: 0.33 g (65%). Anal. Calc. for $C_{13}H_{16}N_4$OPClHg.0.5$CH_2Cl_2$ (553.78): C, 29.28; H, 3.09; N, 10.112. Found: C, 29.08; H, 3.02; N, 9.75%. ESI-MS: m/z: 513.05 (100%, [M+H]$^+$, calc. 513.05), 535.03 (100%, [M+Na]$^+$, calc. 535.04). $^{31}$P {$^1$H} NMR (CDCl$_3$): δ −25.68 (s, $^2J_{Hg-P}$=27.4 Hz). $^1$H NMR (CDCl$_3$): δ 4.40 (12H, m, PTA), 7.39 (2H, t, J=7.6 Hz, $H_2$+$H_4$, $C_6H_4$), 7.51 (1H, t, J=7.5 Hz, $H_3$, $C_6H_4$), 8.23 (1H, d, J=8.1 Hz, $H_5$, $C_6H_4$); $^{13}$C {$^1$H} (CDCl$_3$): δ 52.71 (d, J=45.9 Hz, TPA), 72.76 (d, J=9.5

Hz, PTA), 128.33 (s, $C_4$, $C_6H_4$) 129.84 (s, $C_5$, $C_6H_4$), 131.98 (s, $C_3$, $C_6H_4$), 136.31 (s, $C_2$, $C_6H_4$), signals corresponding to NC=O, $C_1$ and $C_6$ were not observable. Conductivity (acetone): 0.73 µS/cm (neutral) µS/cm.

[($\eta^6$-p-cymene)Ru(($Ph_3P$=N—CO-2-$C_6H_4$)-κ-C,N)Cl]: [Hg(2-$C_6H_4$C(O)N=$PPh_3$)Cl] (0.12 g, 0.2 mmol) and [($\eta^6$-p-cymene)Ru(µ-Cl)Cl]$_2$ (0.13 g, 0.22 mmol) were refluxed in MeCN (20 mL) for 7 days after which a yellow precipitate formed. The pale yellow solid was filtered off and discarded and the orange solution was concentrated to dryness. The solid was dissolved in $CH_2Cl_2$ and filtered through celite. The solvent was removed under reduced pressure to a minimum, followed by addition of $Et_2O$ (~20 mL). The orange solid was filtered off and dried in vacuo. Yield: 0.049 g (37%). Anal. Calc. for $C_{35}H_{33}NOPClRu \cdot 2H_2O$ (687.18): C, 61.18; H, 5.43; N, 2.04. Found: C, 60.97; H, 5.05; N, 2.35%. ESI-MS: m/z: 616.13 (100%, [M−Cl]$^+$, calc. 616.13). $^{31}P$ {$^1H$} NMR (CDCl$_3$): δ 20.63 (s), (d$_6$-DMSO): 21.15 (s); $^1H$ NMR (CDCl$_3$): δ 1.31 (6H, d, J=6.9 Hz, $CH_3$, $\eta^6$-p-cymene), 2.18 (3H, s, $CH_3$, $\eta^6$-p-cymene), 2.95 (1H, sept, J=6.9 Hz, CH, $\eta^6$-p-cymene), 5.37 (2H, d, J=6.0 Hz, CH, $\eta^6$-p-cymene), 5.49 (2H, d, J=6.0 Hz, CH, $\eta^6$-p-cymene), 7.42-7.48 (2H, m, $H_3$+$H_4$), 7.49-7.53 (6H, m, $H_m$), 7.56-7.61 (3H, m, $H_p$), 7.84-7.89 (6H, m, $H_o$), 8.36-8.37 (2H, dd, J=1.4, 8.0 Hz, $H_2$+$H_5$); $^{13}C$ {$^1H$} (CDCl$_3$): δ 19.02 (s, $CH_3$, $\eta^6$-p-cymene), 22.21 (s, $2CH_3$, $\eta^6$-p-cymene), 30.68 (s, CH, $\eta^6$-p-cymene), 80.58 (s, CH, $\eta^6$-p-cymene), 81.32 (s, CH, $\eta^6$-p-cymene), 96.77 (s, C, $\eta^6$-p-cymene), 101.25 (s, C, $\eta^6$-p-cymene), 127.65 (s, $C_3$+$C_4$), 127.92 (s, $C_6$), 128.62-128.74 (d, $C_m$, J=12.4 Hz), 128.91 (s, $C_{ipso}$), 129.51-129.53 (d, J=3.02 Hz, $C_2$+$C_5$), 130.67 (s, $C_3$+$C_4$), 132.19-132.22-(d, $C_p$, J=2.9 Hz), 133.13-133.24 (d, $C_o$, J=9.6 Hz), 138.51-138.72 (d, J=20.6 Hz, C—Ru), 176.26 (s, C=O) ppm. IR (cm$^{-1}$): ν 517 (Ru—N), 1162 (N=P), 1593 (C=O). Conductivity (acetone): 3.76 (neutral) µS/cm.

[($\eta^6$-p-cymene)Ru{(PTA=N—CO-2-$C_6H_4$)-κ-C,N}Cl]: [Hg(2-$C_6H_4$C(O)N=PTA)Cl] (0.1 g, 0.2 mmol) and [($\eta^6$-p-cymene)Ru(µ-Cl)Cl]$_2$ (0.13 g, 0.2 mmol) were refluxed in $CH_2Cl_2$ (20 mL) for 3 days. Subsequently, the solvent was removed to dryness and the yellow solid obtained was dissolved in CHCl$_3$ and filtered through celite. The solvent was removed under reduced pressure to a minimum, followed by addition of $Et_2O$. The yellow solid obtained was collected by filtration and dried in vacuo. Yield: 0.14 g (66%). Anal. Calc. for $C_{23}H_{30}N_4OPClRu$ (546.01): C, 50.59; H, 5.54; N, 10.26. Found: C, 50.32; H, 5.20; N, 10.53%. ESI-MS: m/z: 546.0 (100%, [M−Cl]$^+$, calc. 546.06), 412.0 (100%, [M-p-cymene]$^-$, calc. 412.0). $^{31}P$ {$^1H$} NMR) (CDCl$_3$): δ −16.3 (s), (d$_6$-DMSO): −11.98 (s); $^1H$ NMR (d$_6$-DMSO): δ 0.61 (3H, d, J=6.7 Hz, $CH_3$, $\eta^6$-p-cymene), δ 0.99 (3H, d, J=6.8 Hz, $CH_3$, $\eta^6$-p-cymene), 2.34 (3H, s, $CH_3$, $\eta^6$-p-cymene), 2.24 (1H, sept, J=7.1 Hz, CH, $\eta^6$-p-cymene), 4.47-4.67 (12 h, m PTA), 5.81 (d, 2H, CH, $\eta^6$-p-cymene), 6.06 (d, 1H, J=6.5 Hz, CH, $\eta^6$-p-cymene), 6.74 (d, 1H, J=6.9 Hz, CH, $\eta^6$-p-cymene), 7.11 (t, 1H, J=7.7 Hz, $H_4$), 7.31 (t, 1H, J=7.5 Hz, $H_3$), 7.37 (d, 1H, J=7.5 Hz, $H_5$), 7.81 (d, 1H, J=7.5 Hz, $H_2$); $^{13}C$ {$^1H$} (d$_6$-DMSO): δ 18.70 (s, $CH_3$, $\eta^6$-p-cymene), 19.97 (s, $CH_3$, $\eta^6$-p-cymene), 24.13 (s, $CH_3$, $\eta^6$-p-cymene), 31.00 (s, CH, $\eta^6$-p-cymene), 51.82 (s, PTA), 52.22 (s, PTA), 71.50 (d, J=40.5 Hz, PTA), 86.72 (s, CH, $\eta^6$-p-cymene), 87.22 (s, CH, $\eta^6$-p-cymene), 95.97 (s, CH, $\eta^6$-p-cymene), 100.6 (s, C, $\eta^6$-p-cymene), 127.65 (s, $C_4$), 128.6 (s, $C_5$), 128.6 (s, $C_{ipso}$), 132.6 (s, $C_3$), 138.6-138.7 (d, J=20.6 Hz, C—Ru), 141.1 (s, $C_2$), 183.9 (s, C=O) ppm. IR (cm$^{-1}$): ν 562 (Ru—N), 1314 (N=P), 1582 (C=O). Conductivity (acetone): 25.4 (neutral) µS/cm. Solubility: 0.79 mM or 0.43 mg/mL ($H_2O$).

X-Ray Crystallography

Single crystals of 1 were mounted on a glass fiber in a random orientation. Data collection was performed at RT on a Kappa CCD diffractometer using graphite monochromated Mo—Kα radiation (λ=0.71073 Å). Space group assignments were based on systematic absences, E statistics and successful refinement of the structures. The structures were solved by direct methods with the aid of successive difference Fourier maps and were refined using the SHELXTL 6.1 software package. All non-hydrogen atoms were refined anisotropically. Hydrogen atoms were assigned to ideal positions and refined using a riding model. These data can be obtained free of charge from The Cambridge Crystallographic Data Center via www.ccdc.cam.ac.uk/data_request/cif. (CCDC 1008354) or in the supporting information. Crystals of 1 (xxx prisms with approximate dimensions 0.26×0.24×0.21 mm) were obtained from a solution of 1 in $CH_2Cl_2$ by slow diffusion of $Et_2O$ at RT.

Cell Culture, Inhibition of Cell Growth and Cell Death Analysis

Cell Culture

The human T-cell leukemia Jurkat (clone E6.1) and the prostate carcinoma DU-145 were routinely cultured in RPM 1640 medium supplemented with 5% fetal calf serum (FCS), L-glutamine and penicillin/streptomycin. A549 (lung carcinoma), MiaPaca2 (pancreatic carcinoma), MDA-MB-231 (Triple negative breast carcinoma) and 293T (non-tumoral embryonic kidney cells) were cultured in DMEM medium supplemented with 10% FCS, L-glutamine and penicillin/streptomycin. Media for A549 cells were also supplemented with 2.2 g/l $Na_2CO_3$, 100 µg/ml pyruvate and 5 ml non-essential amino acids (Invitrogen). All these media will be referred as 'complete medium' hereinafter. Cell cultures were maintained in a humidified atmosphere of 95% air/5% $CO_2$ at 37° C.

MTT Toxicity Assays

For toxicity assays cells (5×10$^4$ for Jurkat cells and 10$^4$ for adherent cell lines) were seeded in flat-bottom 96-well plates (100 µl/well) in complete medium. Adherent cells were allowed to attach for 24 h prior to addition of cisplatin or tested compounds. Compounds were added at different concentrations in triplicate. Cells were incubated with cisplatin or compounds for 24 h and then cell proliferation was determined by a modification of the MTT-reduction method. Briefly, 10 µl/well of MTT (5 mg/ml in PBS) was added and plates were incubated for 1-3 h at 37° C. Finally, formazan crystal was dissolved by adding 100 µl/well $^i$PrOH (0.05 M HCl) and gently shaking. The optical density was measured at 570 nm using a 96-well multiscanner autoreader (ELISA). In some experiments total cell number and cell viability were determined by the Trypan-blue exclusion test.

Cell Culture and XTT Assay for RPTC Cells

The human Renal Proximal Tubule Cells (RPTC) a non-tumoral human kidney epithelial cell line (obtained from Lifeline Cell Technology, Frederick, Md., USA) were cultured in Lifeline's RenaLife Medium containing RenaLife LifeFactors with 2.4 mM L-Glutamine, 5 ¼ g/mL rh insulin, 1.0 ¼M epinephrine, 10 nM triiodothyronine, 0.1 ¼ g/mL hydrocortisone hemisuccinate, 10 ng/mL rh EGF, 0.5% FBS and 5 ¼ g/m transferrin PS (all from Lifeline Cell Technology), at 37° C. in a humidified atmosphere of 95% of air and 5% $CO_2$ (University of Hawaii Cancer Center, Honolulu, Hi., USA). For evaluation of cell viability, cells were seeded at a concentration of 5×10^3 cells/well in 90 µl Lifeline's RenaLife complete medium into tissue culture grade 96-well flat bottom microplates (Thermo Scientific BioLite Microwell Plate, Fisher Scientific, Waltham, Mass., USA) and grown for 24 h. Solutions of the compounds were prepared by diluting a freshly prepared stock solution (in H$_2$O) of the corresponding compound in Lifeline's RenaLife complete medium. Afterwards, the intermediate dilutions of the compounds were added to the wells (10 μL) to obtain a final concentration ranging from 0.1 to 200 μM, and the cells were incubated for 24 h. Following 24 h drug exposure, 50 μL of 2,3-Bis-(2-Methoxy-4-Nitro-5-Sulfophenyl)-2H-Tetrazolium-5-Carboxanilide (XTT) (Roche Diagnostics, Indianapolis, Ind., USA) labeling mixture per well was added to the cells at a final concentration of 0.3 mg/ml and incubated for 4 h at 37° C. in a humidified atmosphere of 95% of air and 5% CO$_2$. The optical density of each well (96-well plates) was quantified using EnVision Multilabel Plate Readers (Perkin Elmer, Waltham Mass., USA) at 450 nm wavelength to measure absorbance. The percentage of surviving cells was calculated from the ratio of absorbance of treated to untreated cells. The IC$_{50}$ value was calculated as the concentration reducing the proliferation of the cells by 50% and is presented as a mean (±SE) of at least two independent experiments each with triplicates.

Cell Death Analysis

Apoptosis/necrosis hallmarks of cells treated with compounds 2 and 3 were analyzed by measuring mitochondrial membrane potential and/or exposure of phosphatidylserine. Cells were treated with different concentrations and at different incubation times as indicated in figure legends. In some experiments the general caspase inhibitor z-VAD-fmk was added at 50 μM 1 h before compounds. For mitochondrial membrane potential determination cells (2.5×10$^5$ in 200 μl) after treatment with compounds were incubated at 37° C. for 15 min. in ABB (140 mM NaCl, 2.5 mM CaCl$_2$, 10 mM Hepes/NaOH, pH 7.4) containing 60 mM tetramethylrhodamine ethyl ester (TMRE, Molecular Probes). Phosphatidylserine exposure was quantified by labeling cells with AnnexinV-PE or AnnexinV-DY636 (Invitrogen) after treatment with compounds. AnnexinV was added at a concentration of 0.5 μg/mL and cells were incubated at room temperature for 15 min. In all cases, cells were diluted to 1 ml with ABB to be analyzed by flow cytometry (FACScan, BD Bioscience, Spain).

Intracellular ROS Quantification

Oxidative stress induced by compounds 2 and 3 was analyzed by intracellular staining with the fluorescent probe 2-hydroxiethidium (2-HE, Molecular Probes). After 16 h of culture in the presence of compounds 1-3, cells were incubated with 2 μM 2-HE at 37° C. for 15 min. Red fluorescence produced by reduction of 2-HE to ethidium was quantified in a flow cytometer.

Effect of 2 in the Levels of Proteins of the Bcl-2 Family

Jurkat cells (5×10$^5$ cells/ml) were treated with 2 (1 μM) for 6 h. At the end of incubations total protein extracts from 2×10$^6$ cells were prepared in lysis buffer and samples (50 micrograms/lane) were resolved by SDS-PAGE and transferred onto nitrocellulose membranes. Then, levels of some members of the Bcl-2 family of proteins were analyzed by Western Blot using specific antibodies: Bcl-X$_L$ (Cell Signalling, cat 2764), Bcl-2 (Abcam, Cat AB692), Mcl-1 (Santa Cruz Biotech, cat. SC819), Bim (Calbiochem, cat. 202000), Puma (Cell Signaling, Cat. 4976) and Noxa (Abcam, Cat. 114C307). After incubation with primary antibodies, membranes were incubated with appropriate secondary antibodies conjugated with HRP. Finally, membranes were revealed using a chemiluminiscence substrate (Pierce).

Inhibition of Cathepsin B

Cathepsin B, purified from human liver (Accession #P07858) and substrate Peptide sequence: Z-FR-AMC [AMC=7-amino-4-methylcoumarin] were dissolved on a buffer: 25 mM MES pH 6, 50 mM NaCl, 0.005% Brij35, 5 mM DTT and 1% DMSO with a final concentration of 10 μM. The enzyme solution was delivered into the reaction well. 2 (1% DMSO solution) was delivered into the enzyme mixture by Acoustic technology (Echo550; nanoliter range), incubate for 10 min. at room temp. The substrate solution was delivered into the reaction well to initiate the reaction. The enzyme activity was monitored (Ex/Em=355/460 nm) as a time-course measurement of the increase in fluorescence signal from fluorescently-labeled peptide substrate for 120 min. at room temperature. The data was analyzed data by taking slope (signal/time) of linear portion of measurement. The slope is calculated by using Excel, and curve fits are performed using Prism software.

Interaction of Compounds 1-4, 8, 9, [(η6-p-cymene)Ru (μ-Cl)Cl]2 and Cisplatin with Plasmid (pBR322) DNA by Electrophoresis (Mobility Shift Assay)

10 μL aliquots of pBR322 plasmid DNA (20 μg/mL) in buffer (5 mM Tris/HCl, 50 mM NaClO$_4$, pH=7.39) were incubated with different concentrations of the compounds (1-4, 8, 9, [(η$^6$-p-cymene)Ru(μ-Cl)Cl]$_2$) (in the range 0.25 and 4.0 metal complex:DNAbp) at 37° C. for 20 h in the dark. Samples of free DNA and cisplatin-DNA were prepared as controls. After the incubation period, the samples were loaded onto the 1% agarose gel. The samples were separated by electrophoresis for 1.5 h at 80 V in Tris-acetate/EDTA buffer (TAE). Afterwards, the gel was stained for 30 min. with a solution of GelRed Nucleic Acid stain.

Interaction of Compounds 1-4 with Calf Thymus DNA by Circular Dichroism

Stock solutions (5 mM) of each complex were freshly prepared in water prior to use. The right volume of those solutions was added to 3 ml samples of an also freshly prepared solution of CT DNA (48 μM) in Tris/HCl buffer (5 mM Tris/HCl, 50 mM NaClO$_4$, pH=7.39) to achieve molar ratios of 0.1, 0.25, 0.5, 1.0 and 2.0 drug/DNA. The samples were incubated at 37° C. for a period of 20 h. All CD spectra of DNA and of the DNA-drug adducts were recorded at 25° C. over a range 220-420 nm and finally corrected with a blank and noise reduction. The final data is expressed in molar ellipticity (millidegrees).

DNA Precipitation with Compounds 2 and 3 and Quantification of Ruthenium by ICP-MS Stock solutions of compounds 2 and 3 (4 mM in water) and CT DNA (11.56 mM in 5 mM Tris/HCl, 50 mM NaClO4, pH=7.39) were freshly prepared prior to use. 216 μl of DNA stock solution were diluted in 3.53 mL of buffer and 1.25 mL of compound stock solution were then added to achieve 5 mL final volume at concentrations of 500 μM in DNA and 1 mM in metal compound. Each sample was incubated at 37° C. for a period of 20 h, then cooled down to room temperature and centrifuged at 3000 rpm for 15 min. and at 4000 rpm for extra 40 min. The supernatant was separated and analyzed for CT DNA concentration by CD spectroscopy. The resulting pellet was washed twice with ice-cold ethanol (1 mL), centrifuged at RT for 1 min. at 4000 rpm, dried under high vacuum and analyzed for Ru content by ICP-MS. The total amount of DNA in each sample was 0.92 mg. Every experiment was run in duplicate.

Interaction of Compounds 1-4, 8, 9, and Cisplatin with HSA by Fluorescence Spectroscopy A solution of each compound (8 mM) in DMSO was prepared and ten aliquots of 2.5 μL were added successively to a solution of HSA (10 µM) in phosphate buffer (pH=7.4) to achieve final metal complex concentrations in the range 10-100 µM. The excitation wavelength was set to 295 nm, and the emission spectra of HSA samples were recorded at room temperature in the range of 300 to 450 nm. The fluorescence intensities of all the metal compounds, the buffer and the DMSO are negligible under these conditions. The fluorescence was measured 240 s. after each addition of compound solution. The data were analyzed using the classical Stern-Volmer equation $F_0/F=1+K_{SV}[Q]$.

In Vivo Tests

All animal experiments were performed according to the University of Hawaii Cancer Center regulations and by approval of the responsible authorities (UH IACUC number: A3423-01).

Determination of Lethal Dose (LD) and Maximum Tolerated Dose (MTD) of 2 in Mice 14 female C57/Black 6 from Jackson Laboratory (Bar Harbor, Me. and Sacramento, Calif., USA) ages 8 to 14 weeks and weighing 18-26 g were used for these experiments. Mice were randomized to treatment groups based on their age to ensure equivalent distribution between the groups. At trial end-point the mice were sacrificed and liver, spleen, kidney and blood plasma were collected, and then processed for further analysis. Gross and microscopic evaluations of liver, spleen and kidney were conducted. The weight of 2 treated mice compared and that of vehicle-treated mice as measured twice weekly.

The lethal dose (LD) was determined by injecting once mouse i.p. once 5 mg/kg/day, 10 mg/kg/day, 20 mg/kg/day, 30 mg/kg/day, or 50 mg/kg/day, and one vehicle control with 100 µl Normal Saline (0.9% NaCl)). The dose that killed the mice within 24 hours was set to be lethal dose. The lethal dose was confirmed by administering that dose to a second mouse. The maximum tolerated dose (MTD) was determined by injecting two mice with 5 mg/kg/day, 10 mg/kg/day, or 20 mg/kg/day over 6 days, or 20 mg/kg/every other day over 6 days and one vehicle control mouse with 100 µl Normal Saline (0.9% NaCl). The MTD was confirmed by administering the determined dose to 3 mice over 7 days and three vehicle control mice with 100 µl Normal Saline (0.9% NaCl).

Study of the Effects of 2 in MDA-MB-231 Xenografts in Mice 12 female NOD.CB17-Prkdc scid/J (non-obese diabetic-severe combined immunodeficiency) from Jackson Laboratory (Bar Harbor, Me. and Sacramento, Calif., USA) for the xenograft experiment (ages 8 to 12 weeks and weighing 19-24 g, were used. Each mouse received $5 \times 10^6$ tumor cells subcutaneously without anesthesia. Exponentially growing oestrogen-receptor alpha-negative MDA-MB-231 human breast cancer cells were suspended in 1:1 ratio 50 µl phosphate-buffered saline (PBS; pH 7.4) plus 50 µl of matrigel (BD Biosciences, San Jose, Calif., USA) were injected subcutaneously on both left and right flank of each mice'. The diameter of the tumors was measured once weekly using an electronic digital caliper and the tumor volume (TV) was calculated according to the empirical equation $TV=(a)(b^2) \times \pi/6$ where a=longest dimension; b=largest dimension orthogonal to a. The median volumes of each group were normalized to the initial tumor volume resulting in the relative tumor volume. Each six MDA-MB-231-transplanted animals received compound 2 (5 mg/kg/every other day) or vehicle (0.9% NaCl) intraperitoneally (i.p.) Treatment started when tumors were palpable (about 5-6 mm diameter). To palliate the weight loss observed in the MTD study the mice were fed a 46% fat-adjusted diet (Harlan Teklad, Madison, Wis.), plus HydroGel™ (Harlan Teklad, Madison, Wis.) and received subcutaneous injection of 100 µl Normal Saline (0.9% NaCl) to improve hydration. Mice were randomized to treatment groups based on their starting tumor burden at 12 weeks of age to ensure equivalent distribution between the two groups. At trial end-point the mice were sacrificed and tumors measured again after excision and then processed for further analysis. Histological as well as biochemical evaluations of blood, liver, intestine, kidney, and lung were conducted. Tumor volumes were graphed for (2) treated mice compared to vehicle-treated mice, based on weekly external digital caliper measurements.

Pharmacokinetic Study: Determination of Ruthenium Content in the Organs, Entire Blood, and Plasma Female NOD.CB17-Prkdc scid/J bearing subcutaneous MDA-MB-231 tumors and treated with compound 2 (5 mg/kg/every other day) intraperitoneally were used for pharmacokinetic evaluation of the drug in blood and other tissues. Blood was collected retroorbitally using heparin coated glass capillary into heparinized blood collection vials on ice at time intervals of 30 min, 2 h, 6 h, 24 h and 48 h. after the first dose. The blood samples were centrifuged at 2800 rpm at 4° C. for 15 min. and the supernatant plasma was transferred into 1.5 mL micro-centrifuge tubes and maintained at −80° C. until analysis.

Ruthenium content was determined using Inductively Coupled Plasma-Mass Spectrometry (ICP-MS). Fifty microliter of plasma was transferred into a glass vial and 1 mL of concentrated acid mix (comprising of 75% of 16 N nitric acid and 25% of 12 N hydrochloric acid) was added. The mixture was heated at 90° C. for 5 h. After cooling, the samples were diluted with water, 40 ppb of Indium internal standard was added and analyzed in a Thermo Scientific XSERIES 2 ICP-MS with ESI PC3 Peltier cooled spray chamber with SC-FAST injection loop and SC-4 autosampler. All the elements were analyzed using $He/H_2$ collision-reaction mode. Plasma from control mice was spiked with the test compound to determine the extraction efficiency.

At the end of the study, liver, kidney and tumor of the animals were harvested, weighed and transferred into glass vials. One ml of water was added to each samples and subjected to ultrasonic tissue disruption at 15 W power for 1 min. The tissue homogenates were frozen at −80° C. for 2 h and lyophilized. The lyophilized product was heated at 90° C. with the concentrated acid mix (described above) for 5 h, cooled, diluted with water and analyzed for ruthenium by ICP-MS. Pharmacokinetic estimates were obtained from the plasma concentration-time profiles by noncompartmental analysis using Phoenix WinNonlin 6.1 (Mountain View, Calif.).

What is claimed is:

1. A method for providing a therapeutic benefit for a subject having a cancer, the method comprising administering to the subject a compound of Formula (A), a steroisomer, geometric isomer or pharmaceutically acceptable salt or pro-drug therefor, the compound comprising an arene ruthenium (II) compound with a iminophosphorane ligand:

Formula (A)

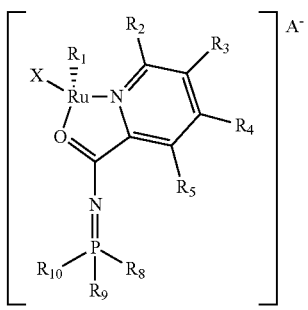

wherein:
- X is a halogen;
- $A^-$ is an anion;
- $R_1$ is an arene;
- $R_2$, $R_3$, $R_4$ an $R_5$ are independently selected from the group consisting of a hydrogen and a $C_1$-$C_5$ alkyl;
- $R_8$, $R_9$ and $R_{10}$ are independently selected from a $C_1$-$C_5$ alkyl, an arene, and a cyclic amine.

2. The method as recited in claim 1, wherein $R_1$ comprises a six-carbon aromatic ring.

3. The method as recited in claim 1, wherein $R_1$ comprises a six-carbon aromatic ring, X is chlorine, $A^-$ is chloride, and each of $R_2$, $R_3$, $R_4$ an $R_5$ are hydrogens.

4. The method as recited in claim 1, wherein $R_1$ is a p-cymene.

5. The method as recited in claim 1, wherein X is chlorine, $A^-$ is chloride, $R_1$ is p-cymene, each of $R_2$, $R_3$, $R_4$ and $R_5$ are hydrogens and $R_8$, $R_9$ and $R_{10}$ are phenyls.

6. The method as recited in claim 1, wherein X is chlorine, $A^-$ is $PF_6^-$, $R^1$ is p-cymene, each of $R_2$, $R_3$, $R_4$ and $R_5$ are hydrogens and $R_8$, $R_9$ and $R_{10}$ are phenyls.

7. The method as recited in claim 1, wherein $R_8$, $R_9$ and $R_{10}$ are phenyls.

8. The method as recited in claim 1, wherein each of $R_2$, $R_3$, $R_4$ and $R_5$ are hydrogens.

9. The method as recited in claim 1, wherein $R_1$ comprises a six-carbon aromatic ring, X is chlorine, $A^-$ is chloride, and $R_8$, $R_9$ and $R_{10}$ are phenyls.

10. The method as recited in claim 1, wherein $R_1$ comprises a six-carbon aromatic ring and $R_8$, $R_9$ and $R_{10}$ are phenyls.

* * * * *